(12) United States Patent
Kaushal et al.

(10) Patent No.: US 7,561,269 B2
(45) Date of Patent: Jul. 14, 2009

(54) OPTICAL MEASUREMENT SYSTEM WITH SYSTEMATIC ERROR CORRECTION

(75) Inventors: Sanjeev Kaushal, San Jose, CA (US); Sairam Sankaranarayanan, Fremont, CA (US); Kenji Sugishima, Tokyo (JP)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 11/956,751

(22) Filed: Dec. 14, 2007

(65) Prior Publication Data

US 2009/0153842 A1 Jun. 18, 2009

(51) Int. Cl.
*G01N 21/00* (2006.01)
*G01B 11/00* (2006.01)
*G01B 21/88* (2006.01)

(52) U.S. Cl. .................... 356/394; 356/237.5; 356/625; 250/559.22

(58) Field of Classification Search ......... 356/601–625, 356/509, 369, 237.2–237.5, 392–394; 250/559.19, 250/559.22, 492.22; 438/14–18; 430/50, 430/53, 55; 700/121, 95–96
See application file for complete search history.

(56) References Cited

U.S. PATENT DOCUMENTS

| | | | | |
|---|---|---|---|---|
| 4,585,348 A * | 4/1986 | Chastang et al. ............ 356/369 |
| 4,923,301 A * | 5/1990 | White ........................ 356/509 |
| 5,274,433 A * | 12/1993 | Madey et al. ................ 356/155 |
| 6,124,142 A * | 9/2000 | Fujino et al. .................. 438/18 |
| 6,792,328 B2 * | 9/2004 | Laughery et al. ............ 700/121 |
| 6,907,107 B1 * | 6/2005 | Wallis et al. .................. 378/83 |
| 6,972,201 B1 * | 12/2005 | Subramanian et al. ........ 438/14 |
| 7,064,829 B2 | 6/2006 | Li et al. |
| 7,092,110 B2 * | 8/2006 | Balasubramanian et al. 356/625 |
| 7,271,902 B2 | 9/2007 | Li et al. |
| 7,321,426 B1 * | 1/2008 | Poslavsky et al. ........... 356/369 |
| 2003/0002043 A1 * | 1/2003 | Abdulhalim et al. ........ 356/400 |
| 2006/0244966 A1 | 11/2006 | Li et al. |
| 2008/0037017 A1 | 2/2008 | Li et al. |

* cited by examiner

*Primary Examiner*—Sang Nguyen
(74) *Attorney, Agent, or Firm*—Oblon, Spivak, McClelland, Maier & Neustadt, P.C.

(57) ABSTRACT

An optical measurement system and wafer processing tool for correcting systematic errors in which a first diffraction spectrum is measured from a standard substrate including a layer having a known refractive index and a known extinction coefficient by exposing the standard substrate to a spectrum of electromagnetic energy. A tool-perfect diffraction spectrum is calculated for the standard substrate. A hardware systematic error is calculated by comparing the measured diffraction spectrum to the calculated tool-perfect diffraction spectrum. A second diffraction spectrum from a workpiece is measured by exposing the workpiece to the spectrum of electromagnetic energy, and the measured second diffraction spectrum is corrected based on the calculated hardware systematic error to obtain a corrected diffraction spectrum.

30 Claims, 15 Drawing Sheets

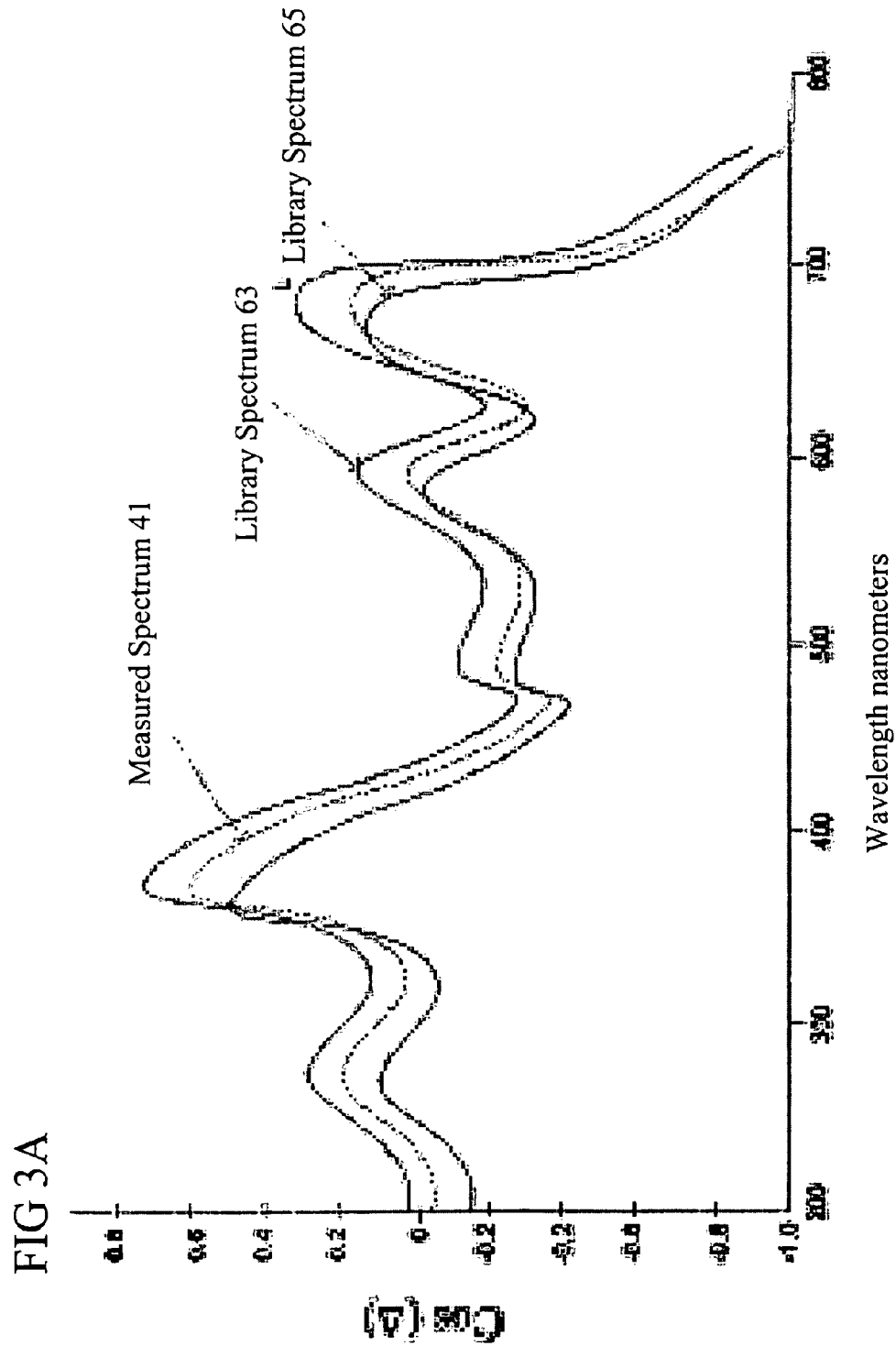

Fig. 6

| Optical component | Mueller matrix |
|---|---|
| 1) A perfect linear polarizer with horizontal transmission axis | $\frac{1}{2}\begin{bmatrix} 1 & 1 & 0 & 0 \\ 1 & 1 & 0 & 0 \\ 0 & 0 & 0 & 0 \\ 0 & 0 & 0 & 0 \end{bmatrix}$ |
| 2) A partial linear polarizer with horizontal transmission axis and attenuation coefficient $\alpha$ | $\frac{1}{2}\begin{bmatrix} 1+\alpha & 1-\alpha & 0 & 0 \\ 1-\alpha & 1+\alpha & 0 & 0 \\ 0 & 0 & 2\sqrt{\alpha} & 0 \\ 0 & 0 & 0 & 2\sqrt{\alpha} \end{bmatrix}$ |
| 3) Reflection sample characterized by the ellipsometric quantities $\Psi$ and $\Delta$ | $\begin{bmatrix} 1 & -\cos 2\psi & 0 & 0 \\ -\cos 2\psi & 1 & 0 & 0 \\ 0 & 0 & \sin 2\psi \cos\Delta & \sin 2\psi \sin\Delta \\ 0 & 0 & \sin 2\psi \sin\Delta & \sin 2\psi \cos\Delta \end{bmatrix}$ |
| 4) A compensator with horizontal fast axis, a retardance of $\Delta_c$ and a relative amplitude change $\Psi_c$ | $\begin{bmatrix} 1 & \cos 2\psi_c & 0 & 0 \\ \cos 2\psi_c & 1 & 0 & 0 \\ 0 & 0 & \sin 2\psi_c \cos\Delta_c & \sin 2\psi_c \sin\Delta_c \\ 0 & 0 & \sin 2\psi_c \sin\Delta_c & \sin 2\psi_c \cos\Delta_c \end{bmatrix}$ |
| 5) A depolarizing component with degree of polarization $\beta$ | $\begin{bmatrix} 1 & 0 & 0 & 0 \\ 0 & \beta & 0 & 0 \\ 0 & 0 & \beta & 0 \\ 0 & 0 & 0 & \beta \end{bmatrix}$ |
| 6) A Rotation matrix to transform to a rotated frame of reference. The new frame is rotated through an angle $\theta$ relative to the original frame of reference | $\begin{bmatrix} 1 & 0 & 0 & 0 \\ 0 & \cos 2\theta & \sin 2\theta & 0 \\ 0 & \sin 2\theta & \cos 2\theta & 0 \\ 0 & 0 & 0 & 1 \end{bmatrix}$ |

Fig. 8

| Error sources | Jacobian $\begin{pmatrix} \psi \\ \Delta \end{pmatrix}$ |
|---|---|
| $\dfrac{\partial}{\partial P}$ | $\begin{pmatrix} \dfrac{\sin 2\psi}{\sin 2P} \\ 0 \end{pmatrix}$ |
| $\dfrac{\partial}{\partial A}$ | $\begin{pmatrix} \dfrac{(1-\cos 2P \cos 2\psi)\cos\Delta}{\sin 2P} \\ \dfrac{(\cos 2P - \cos 2\psi)\sin\Delta}{\sin 2P \sin 2\psi} \end{pmatrix}$ |
| $\dfrac{\partial}{\partial D}$ | $\begin{pmatrix} \dfrac{(\cos 2P - \cos 2\psi)(1-\cos 2P \cos 2\psi)}{2\sin 2\psi \sin^2 2P} \\ -\dfrac{(1-\cos 2P \cos 2\psi)^2 \cos\Delta}{\sin^2 2P \sin^2 2\psi \sin\Delta} \end{pmatrix}$ |
| $\dfrac{\partial}{\partial \alpha_p}$ | $\begin{pmatrix} \dfrac{\cos 2P \sin 2\psi}{\sin^2 2P} \\ -\dfrac{2\cos\Delta}{\sin^2 2P \sin\Delta} \end{pmatrix}$ |
| $\dfrac{\partial}{\partial \alpha_a}$ | $\begin{pmatrix} \dfrac{(\cos 2P - \cos 2\psi)(1-\cos 2P \cos 2\psi)}{\sin 2\psi \sin^2 2P} \\ -\dfrac{2(1-\cos 2P \cos 2\psi)^2 \cos\Delta}{\sin^2 2P \sin^2 2\psi \sin\Delta} \end{pmatrix} |

Fig. 10

| Error sources | Jacobian $\begin{pmatrix} \psi \\ \Delta \end{pmatrix}$ |
|---|---|
| $\dfrac{\partial}{\partial P}$ | $\begin{pmatrix} -\sin 2\Psi \\ 0 \end{pmatrix}$ |
| $\dfrac{\partial}{\partial A}$ | $\dfrac{1}{z_c}\begin{pmatrix} -x_c \cos 2\Psi (1+\cos 2\Psi)\sin\Delta + z_c \cos\Delta \\ 2x_c(1+\cos 2\Psi)\cos\Delta + 2z_c \cos 2\Psi \sin\Delta \end{pmatrix}$ |
| $\dfrac{\partial}{\partial C}$ | $\dfrac{-1}{z_c}\begin{pmatrix} x_c \cos 2\Psi(1+\cos 2\Psi)\sin\Delta - 2z_c \cos\Delta \\ \dfrac{2x_c(1+\cos 2\Psi)\cos\Delta + 4z_c \cos 2\Psi \sin\Delta}{\sin 2\Psi} \end{pmatrix}$ |
| $\dfrac{\partial}{\partial D}$ | $\begin{pmatrix} 0 \\ 0 \end{pmatrix}$ |
| $\dfrac{\partial}{\partial \alpha_p}$ | $\begin{pmatrix} -\cos 2\Psi \sin 2\Psi \\ 0 \end{pmatrix}$ |
| $\dfrac{\partial}{\partial \alpha_a}$ | $\begin{pmatrix} \dfrac{x_c}{z_c}\cos 2\Psi \sin 2\Psi \cos\Delta \sin\Delta \\ 2\dfrac{x_c}{z_c}\cos^2\Delta \end{pmatrix}$ |

OPTICAL MEASUREMENT SYSTEM WITH SYSTEMATIC ERROR CORRECTION

CROSS REFERENCE TO RELATED APPLICATIONS

This application is related to entitled "Methods of Correcting Systematic Error in a Metrology System" filed on Dec. 14, 2007 as U.S. Ser. No. 11/956,777.

BACKGROUND OF THE INVENTION

1. Field of the Invention

The field of invention relates generally to optical measurement tools and, more particularly, to a method for correcting systematic error in such tools.

2. Description of the Related Art

Characteristics of semiconductor devices are directly dependent on the shapes and dimensions of one or more layers and/or features of a device. During a fabrication process, a drift in one or more process parameters can result in deviations on the device critical dimensions (CDs), potentially rendering the devices useless. Optical metrology has been traditionally employed to monitor semiconductor fabrication processes. Scanning Electron Microscopy (SEM) has been in the forefront in this area. Commonly referred to as CD-SEM (Critical Dimension Scanning Electron Microscopy), this form of optical metrology poses two major disadvantages. One is that the measurement process is destructive and the other is that it cannot be used in-situ, which prohibits its deployment in integrated metrology.

Optical digital profilometry (ODP) has emerged recently as a metrology system that overcomes the above mentioned short-comings of CD-SEM. The basis of ODP is that quantities resulting from a measurement of a layer, a series of stacked layers, or a device structure with a specific profile characterized by specific material properties, layer thicknesses, and/or CDs are unique to that profile. A library of profiles may be created to represent a set of layers and/or device structures, each with its own unique profile.

A library of films and/or profiles with corresponding predicted spectra can be generated using scatterometry. Scatterometry is an optical measurement technology based on an analysis of one or more wavelengths of light scattered from a layer or array of layers and/or device structures. The device structures may be a series of photoresist gratings or arrays of contact holes on a test sample. Scatterometry is a model-based metrology that determines measurement results by comparing measured light scatter against a model of theoretical spectra. A profile of the given test sample is extracted by searching the library for a match of the measured spectra with theoretical spectra in the library and once a match is found, the corresponding profile is taken to be the profile of the given sample.

The methodology of ODP is computer-intensive since it involves generation of one or more libraries of predicted spectra as well as searching of a master library, or one or more derivatives of the master library, for matching spectra. The size of the library generally governs the resolution of the final result. Generation of one or more libraries typically involves repeating a prediction process for a series of layers and/or profile shapes to create a series of corresponding scatterometry spectra. Prediction of scatterometry spectra is provided by a numerical solution of governing Maxwell's equations. Each layer, stacked layer, and/or profile is translated into a theoretical model that factors in physical parameters such as optical properties of the semiconductor materials. Maxwell's equations are applied with appropriate boundary conditions to form a system of equations that are numerically solved for example using Rigorous Coupled Wave Analysis (RGWA).

Measurements taken of the same sample on multiple scatterometry tools or optical metrology systems yield different scatterometry spectra, since each tool is prone to tool specific systematic error sources. Each master library, and/or one or more derivatives of each master library, is hardware dependent because measured spectra for each profile are affected by the tool specific systematic error sources. As a result, the master library and/or derivatives of each master library needs to be regenerated for each metrology tool. Library regeneration is a time consuming process that may impact availability of a scatterometry tool in a manufacturing environment. In many cases, the scatterometry tool is used as in-situ process control for one or more semiconductor manufacturing processes, such as lithography or dry-etch. The manufacture of semiconductors is an extremely expensive process and a reduction in scatterometry tool availability is expensive, if not intolerable.

BRIEF DESCRIPTION OF THE DRAWINGS

The present invention is illustrated by way of example and not as a limitation in the figures of the accompanying drawings, in which

FIG. 3A illustrates, according to one embodiment of the invention, a measured diffraction spectrum graph compared to diffraction spectra graphs of instances in a profile library;

FIG. 6 is a table of Mueller matrices for different components of an ellipsometer;

FIG. 8 is a table of detailed expressions for Jacobians with respect to an attenuation coefficient $\alpha_a$;

FIG. 10 is a table showing first derivative expressions for a rotating compensating polarizer analyzer elllipsometer;

DETAILED DESCRIPTION

Methods for correcting systematic error in a metrology system is disclosed in various embodiments. However, one skilled in the relevant art will recognize that the various embodiments may be practiced without one or more of the specific details, or with other replacement and/or additional methods, materials, or components. In other instances, well-known structures, materials, or operations are not shown or described in detail to avoid obscuring aspects of various embodiments of the invention. Similarly, for purposes of explanation, specific numbers, materials, and configurations are set forth in order to provide a thorough understanding of the invention. Nevertheless, the invention may be practiced without specific details. Furthermore, it is understood that the various embodiments shown in the figures are illustrative representations and are not necessarily drawn to scale.

Reference throughout this specification to "one embodiment" or "an embodiment" means that a particular feature, structure, material, or characteristic described in connection with the embodiment is included in at least one embodiment of the invention, but do not denote that they are present in every embodiment. Thus, the appearances of the phrases "in one embodiment" or "in an embodiment" in various places throughout this specification are not necessarily referring to the same embodiment of the invention. Furthermore, the particular features, structures, materials, or characteristics may be combined in any suitable manner in one or more embodiments. Various additional layers and/or structures may be included and/or described features may be omitted in other embodiments.

Various operations will be described as multiple discrete operations in turn, in a manner that is most helpful in understanding the invention. However, the order of description should not be construed as to imply that these operations are necessarily order dependent. In particular, these operations need not be performed in the order of presentation. Operations described may be performed in a different order than the described embodiment. Various additional operations may be performed and/or described operations may be omitted in additional embodiments.

There is a general need for a method of using a common set of library spectra across a plurality of metrology tools. By providing a method of using a common set of library spectra across a number of metrology tools, such as optical metrology tools, an extensive yet common set of spectra may be used to identify a layer, a plurality of stacked layers, or structure profiles on substrates without the need for developing a customized library for each individual metrology tool.

Figure 1:
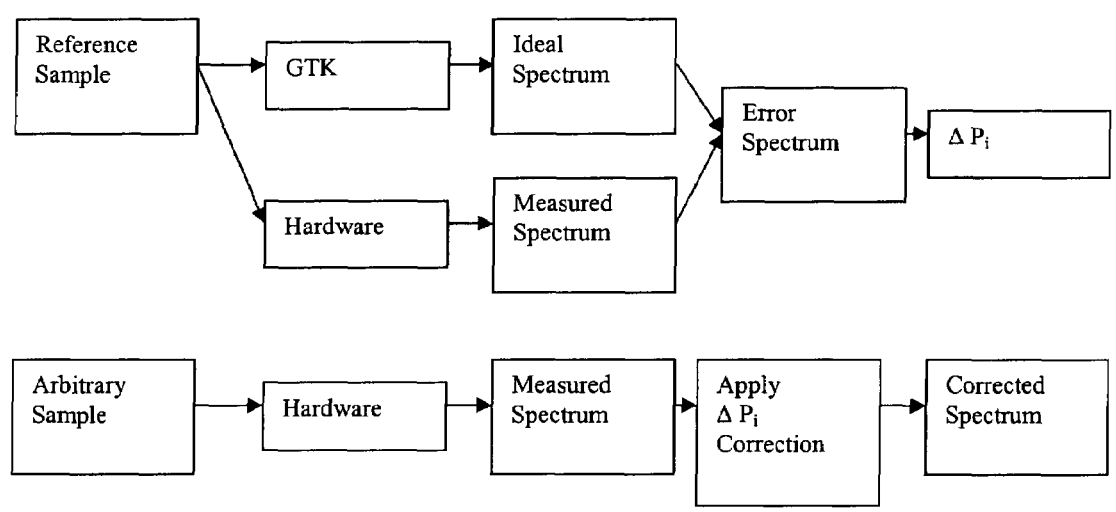
FIG. 1 is a process schematic according to one embodiment of the invention for correction of optical metrology data.

One embodiment of a method of identifying a sample profile, with a metrology tool is illustrated in the flowchart of FIG. 1. As shown in FIG. 1, a reference sample or golden sample is utilized to provide both an "ideal" spectrum (based on modeling of the optical performance of the metrology tool) and a "measured" spectrum (measured by the metrology tool). The reference sample is a substrate having known optical and structural properties such for example a known refractive index and a known extinction coefficient by which its diffraction spectrum is known. For example, the reference sample can be a silicon substrate with a known thickness of thermally-grown silicon dioxide.

As shown in FIG. 1, the ideal spectrum and the measured spectrum are compared to determine an error spectrum representing hardware errors in the metrology tool from a "perfect" metrology tool. As used herein, perfect denotes what would be considered to be derived from a metrology tool in which there were no imperfections in the optical components. From the error spectrum, hardware error $\Delta P_i$ is derived. Once obtained the hardware error $\Delta P_i$ permits measurements of subsequent samples without known optical properties to have their measured spectrum corrected for the hardware error $\Delta P_i$.

For example, FIG. 1 shows (in the lower half) a methodology by which an arbitrary sample is measured by the metrology tool, producing a measured spectrum for that arbitrary sample. The hardware error $\Delta P_i$ is applied to the measured spectrum to produce a corrected spectrum. From the corrected spectrum, library matching to determine the optical structure for the corrected spectrum can be utilized to ascertain for the arbitrary sample its physical dimensions and/or optical properties such as refractive index and extinction coefficient.

Figure 2:
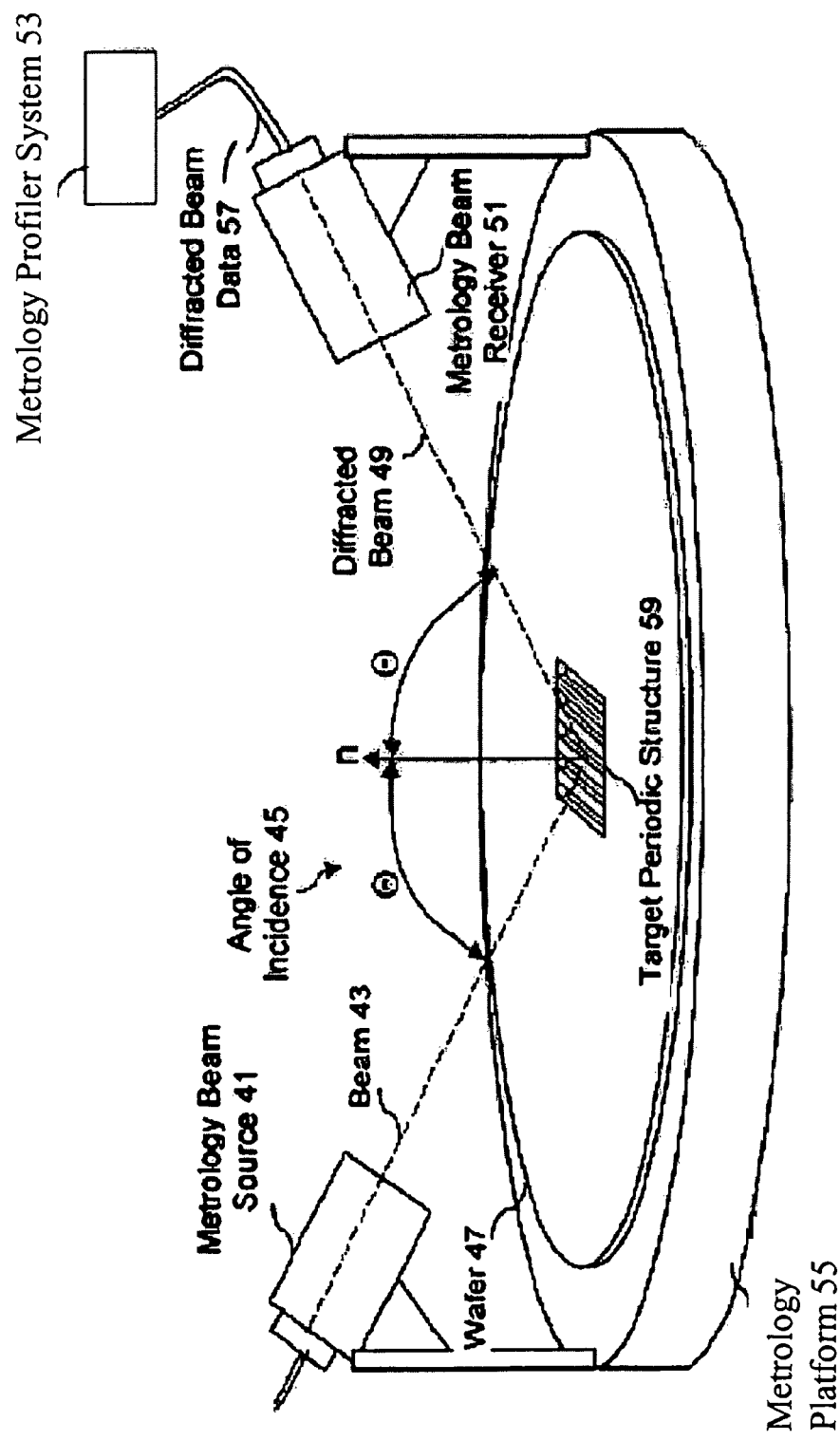
FIG. 2 is an illustration of the use of optical metrology to measure the diffracted spectra off integrated circuit periodic structures according to one embodiment of the invention.

Now turning to a more specific illustration of the methodology and systems for the present invention, FIG. 2 is an illustration of a standard optical metrology to measure diffraction spectra from integrated circuit periodic structures. The optical metrology system 40 includes a metrology beam source 41 projecting a beam 43 at a target periodic structure 59 of a workpiece or wafer 47 mounted on a metrology platform 55. The metrology beam source 41 can include for example a white color or multi-wavelength light source, such as an xenon lamp or similar light source for providing a multi-wavelength region of light, such as for example, 190 nm to 830 nm or from 135 nm to 33 µm, which are wavelength ranges being used in commercial optical metrology tools. The metrology beam 43 is projected at an incidence angle theta (θ) towards the target periodic structure 59. The light reflected from the workpiece or wafer 47 will become elliptically polarized having an amplitude and phase that are indicative of the physical properties of the workpiece or wafer 47. The diffracted beam 49 is measured by a metrology beam receiver 51. The diffracted beam data 57 is transmitted to a metrology profiler system 53. The metrology beam receiver 51 and the metrology profiler system 53 can transmit and converge light into a spectroscope to be converted into electrical signals for subsequent computation by an algorithm to provide an output measurement for example producing a psi-delta spectrum.

The metrology profiler system 53 stores the measured diffracted beam data 57. If the measured diffracted beam data 57 is data from the reference sample, this data will be stored and compared to the "ideal" spectrum, as discussed above, to produce the hardware error $\Delta P_i$. If the measured diffracted beam data 57 is data from the arbitrary sample, this data will be adjusted by the hardware error $\Delta P_i$ to produce a corrected spectrum. The corrected spectrum is compared against a library of calculated diffracted beam data representing varying combinations of profile parameters of a target periodic structure and resolution. A best match routine is used to select which library spectrum most closely matches the corrected spectrum. The profile and associated critical dimensions of the selected library spectrum are assumed to correspond for example to a cross-sectional profile and to critical dimensions of the arbitrary sample.

Figure 3B:
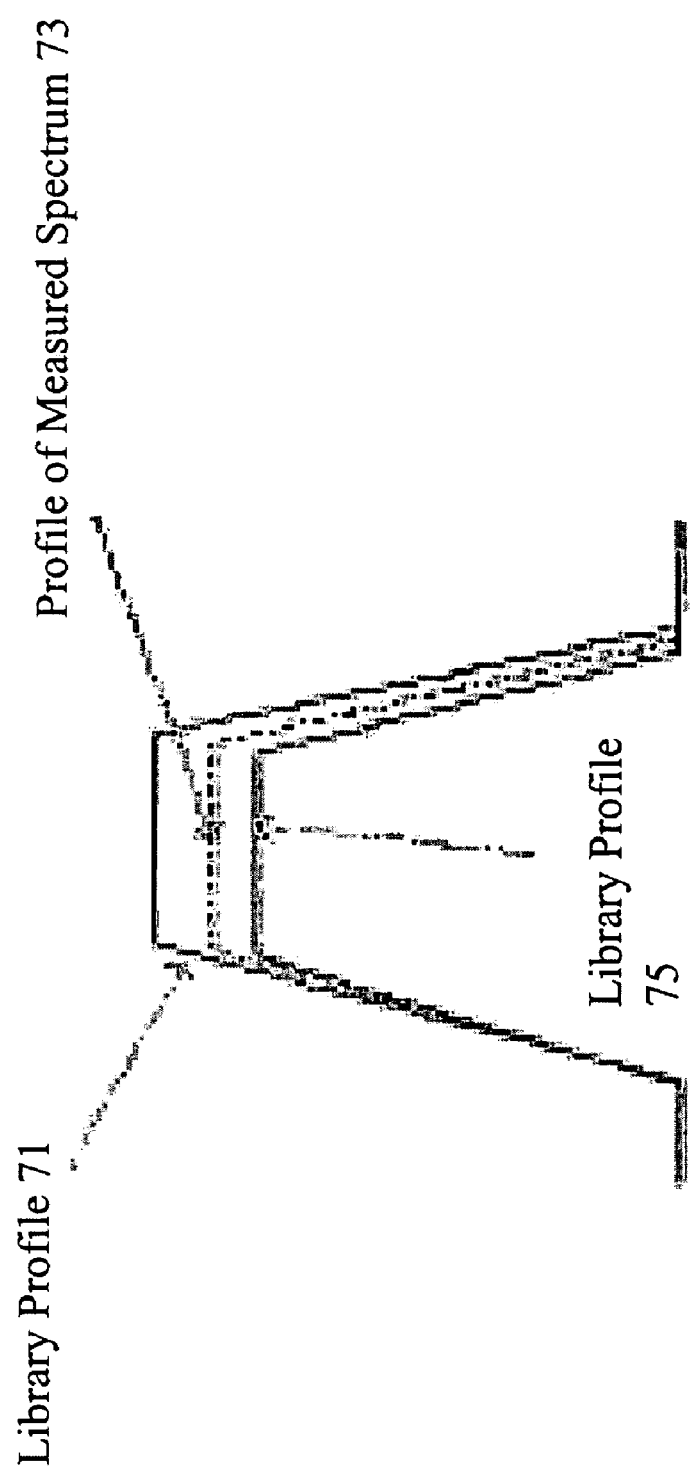
FIG. 3B illustrates, according to one embodiment of the invention, a structure profile of a measured periodic structure compared to profiles of instances in a profile library.

While illustrated here with a spectral ellipsometer, the present invention is not limited to spectral ellipsometers can be used with other optical metrology tools. For example, the optical metrology system 40 may also utilize a reflectometer, a laser ellipsometer, or other optical metrology device to measure the diffracted beam or spectrum. Furthermore, the reference sample and the arbitrary sample need not have similar optical and structural properties, as the purpose of the reference sample is to correct or account for deviations of the metrology tool from "perfect" conditions. The library match routine would use general information about the arbitrary sample to better determine which library spectrum to compare to the corrected spectrum. FIGS. 3A and 3B illustrate these principles.

FIG. 3A illustrates an ellipsometric measurement depicting measured diffraction spectrum graph compared to diffraction spectra graphs of instances in a profile library. The wavelength in nanometers (nm) is shown in the X-axis (referred to as "PSI" data), and cosine delta Δ (referred to as "DELTA" data and depicted in FIG. 2 as 2θ) of the diffraction spectrum is shown in the Y-axis. A profile library is created with ranges of CD's and other profile parameters of structures in a wafer. The number of instances of the profile library is a function of the combinations of the various CD's and other profile parameters at the specified resolution. For example, the range of the top CD for a structure may be from 100 to 300 nm and the specified resolution may be 10 nm. In combination with the other profile parameters of the structure, one or more instances of the profile library are created starting at 100 nm top CD and for every 10 nm increment thereafter until 300 nm. For example, instances of a profile library for trapezoidal profiles may have diffraction spectra and profile parameters including a top CD, a bottom CD, and a height. In FIG. 3A, library spectrum 63 representing a set of the profile parameters at a given resolution and another library spectrum 65 with a different set of profile parameters at the same resolution are illustrated. The corrected measured spectrum 61 (adjusted for hardware error APE) is in close proximity to the library spectra 63 and 65. One aspect of the present invention (as discussed above) is to determine a structural profile that best corresponds to the corrected measured diffraction spectrum 61. FIG. 3B illustrates this principle.

FIG. 3B illustrates a structural profile of a measured periodic structure compared to profiles of instances in a profile library. A library profile 71 of a trapezoidal structure is illustrated with another similar library profile 75. A corrected measured diffraction spectrum corresponds to a profile 73, shown as a dotted line, with profile parameters that are in close proximity to library profiles 71 and 75. As an example, assume that library profile 71 corresponds to library spectrum 63 and that library profile 75 corresponds to library spectrum 65. As depicted in FIG. 3A, neither library spectrum 63 or 65 exactly matches the corrected measured spectrum 61. As such, a selection based on a "best match" algorithm would be used to select the closest match.

Figure 4:
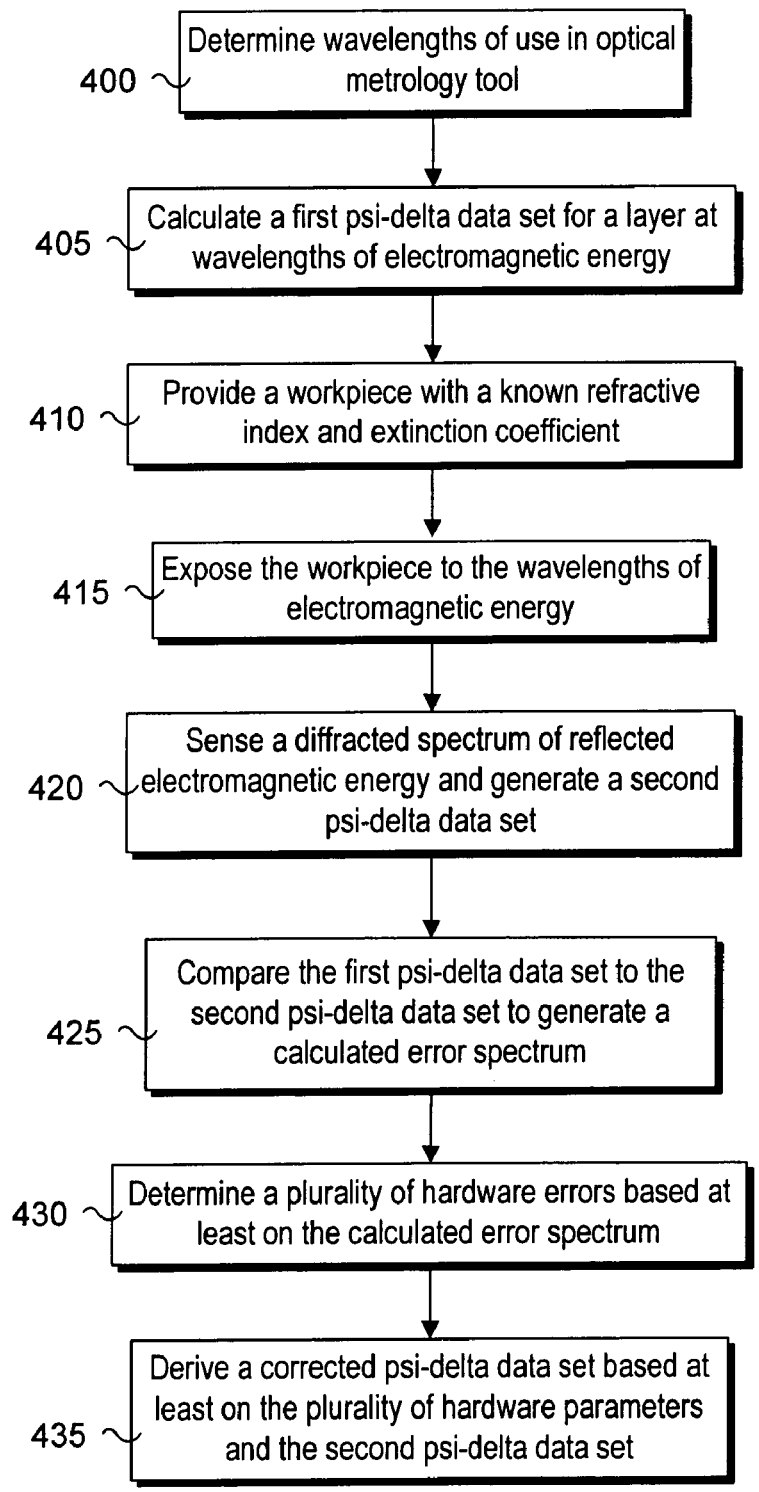
FIG. 4 is a flowchart describing one embodiment of a method of correcting systematic error in an optical metrology system.

FIG. 4 is a flowchart describing one embodiment of a method of correcting systematic error in an optical metrology system 40 through optical digital profilometry (ODP). One example of a optical metrology system 40 used in ODP is an ellipsometer, which is configured to characterize a planar profile or non-planar profile of a substrate surface, single layer thin film, or a stacked layer of thin films ranging from a few angstroms or tenths of a nanometer to several micrometers with excellent accuracy and precision in a contact-less and non-destructive manner.

The process may be initiated (element 400) by ascertaining the wavelengths of use in the optical metrology tool. One example of an optical metrology system 40 is an ellipsometry-based optical measurement and characterization system such as a Therma-Wave Opti-Probe 7341 XP or an Ultra-II CD manufactured by Rudolph Technologies. Another optical metrology system suitable for the invention is the Archer 100 Advanced Optical Overlay Metrology tool manufactured by KLA-Tencor. Another optical metrology system suitable for the invention is the Spectroscopic Ellipsometer manufactured by SOPRA. A first psi-delta data set (i.e., a diffraction spectrum) is calculated using the wavelength of electromagnetic energy in element 405 to produce the "ideal" spectrum noted above. In one embodiment, the first psi-delta data set is calculated through solution of applicable Maxwell Equations. The first psi-delta data set would correspond to the "tool-perfect" spectrum discussed above. The Maxwell Equations are applied with appropriate boundary conditions and the system of equations are solved using for example in one embodiment rigorous coupled wave analysis (RCWA). Other solution techniques can be used in the present invention.

A workpiece, having a substrate and a layer having a known refractive index and a known extinction coefficient is provided in element 410. The layer on the substrate has a known profile. The known profile may be a patterned substrate surface, a planar single layer film, a non-planar single layer film, a planar stacked layer film, or a non-planar stacked layer film. In one embodiment, the known profile on the first substrate is a repeating pattern of three-dimensional bodies, such as multi-gate transistor bodies, formed on the surface of the first substrate. In another embodiment, the known profile on the first substrate is a repeating pattern of three-dimensional periodic gratings formed in a single layer resist or other dielectric film. In a further embodiment, the known profile on the first substrate is a repeating pattern of a three dimensional periodic grating formed in a multi-layer stacked resist or other dielectric film.

In element 415, the workpiece having known optical and structural properties is exposed to the electromagnetic energy from the metrology tool. A diffraction spectrum is sensed or measured by a metrology beam receiver 51 (element 420) and a second psi-delta data set is generated based on the measurement.

The first psi-delta data set and the second psi-delta data set are compared (element 425) to generate a calculated error spectrum. In element 430, the hardware error $\Delta P_i$ is derived based at least on the plurality of hardware parameters and the comparison of the first and second psi-delta data set. The plurality of hardware error parameters $\Delta P_i$ are determined based at least on the calculated error spectrum. The hardware parameters may be specific to the type of metrology used and may include at least one of analyzer azimuth error, polarizer azimuth error, wire grid radius, wire grid spacing, wire conductivity, and numerical aperture in order to identify error terms associated with imperfections in each of the associated components. A value of each hardware parameter is expected to be unique to each optical metrology system 40 and may change in a step function manner due to component replacement as a result of a maintenance event, or the hardware error may change incrementally due to a drift in a characteristic of a hardware component.

The hardware error $\Delta P_i$ accounts for instrument error and provides a mechanism by which a more accurate measure of the structural properties such as CD can be derived. In other words, the present invention for the first time permits one to decouple instrument errors from the measured data, and as a result permits libraries of comparison data between optical measurements and known physical structures to be used across multiple processing machines.

Figure 5:
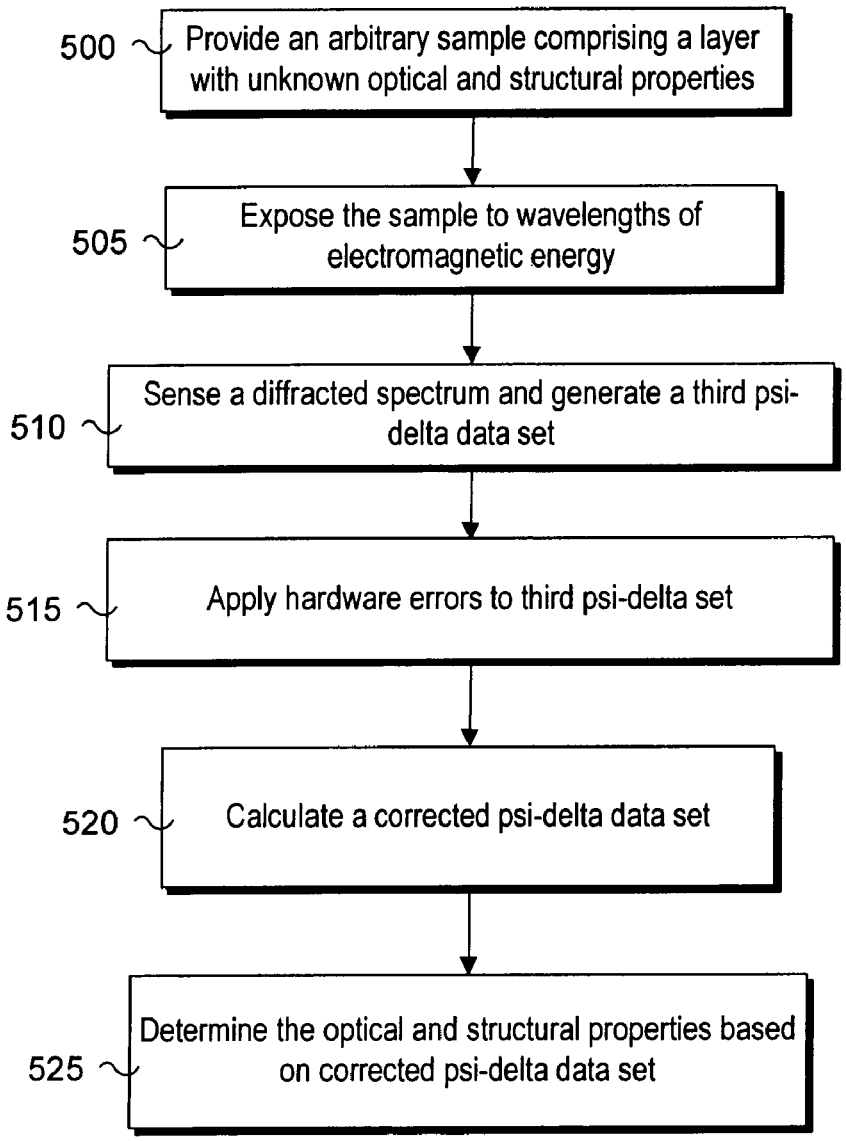
FIG. 5 is a flowchart describing another embodiment of a method of correcting systematic error in an optical metrology system.

FIG. 5 is a flowchart describing another embodiment of a method of correcting systematic error in an optical metrology system based on having determined the hardware error $\Delta P_i$ for the optical metrology tool being used. In element 500, an arbitrary sample of unknown optical properties is provided. In element 505, the sample is exposed to electromagnetic energy from the metrology tool. A diffraction spectrum is sensed or measured by a metrology beam receiver 51 (element 510) and a third psi-delta data set is generated based on the measurement. In element 515, the hardware error $\Delta P_i$ is applied to the third psi-delta data set to produce a corrected psi-delta data set (element 520). In element 525, the corrected psi-delta data set is used to determine the optical and structural properties of the arbitrary sample by matching the corrected psi-delta data set to a library spectrum with known optical and structural properties. The procedures outlined above with regard to FIGS. 3A and 3B can be utilized here.

In another embodiment, a method of identifying a sample profile, using a spectrum library, with a metrology tool includes providing a substrate with an unknown profile, measuring with the metrology tool a diffraction spectrum, and correcting the measured diffraction spectrum based on hardware errors $\Delta P_i$. In this embodiment, the corrected measured diffraction spectrum is only considered a "partially corrected" spectrum, as sample artifacts such as depolarization effects are not accounted for by the hardware errors $\Delta P_i$. The partially corrected spectrum is analyzed in comparison to the spectrum library to determine an interim spectrum match. A depolarization factor is computed based at least in part on a numerical aperture of the metrology tool, and the partially corrected spectrum is modified using the depolarization factor to form an iterate spectrum. The iterate spectrum is analyzed in comparison to the spectrum library to determine an iterate spectrum match. One example of a comparison algorithm suitable for the present invention is a probabilistic global search lausanne algorithm. This process referred to herein as the "iterative approach" will be discussed in more detail later and represents another significant advance in the art.

While illustrated above with respect to critical dimension determination and process control such as for example a developed photoresist line or an etched gate metal line, the present invention is in general applicable any metrology tool using an optical technique and feedback or feed forward for process control. Specific but non-limiting application areas for the invention are discussed in more detail below.

In semiconductor processing and other areas, a lithographic apparatus is used to apply a desired pattern onto a surface (e.g. a target portion of a substrate). Lithographic projection apparatus can be used, for example, in the manufacture of integrated circuits (ICs) or in thin film transistor devices such as with flat panel display manufacture. In these cases, the patterning device may generate a circuit pattern corresponding to an individual layer of the IC, and this pattern can be imaged onto a target portion (e.g. including one or more dies and/or portion(s) thereof) on a substrate (e.g. a wafer of silicon or other semiconductor material) that has been coated with a layer of radiation-sensitive material (e.g. a photoresist).

In general, a single wafer can contain a whole matrix or network of adjacent target portions that are successively irradiated via the projection system (e.g. one at a time). Among current apparatus that employ patterning by a mask on a mask table, a distinction can be made between two different types of machine. In one type of lithographic projection apparatus, each target portion is irradiated by exposing the entire mask pattern onto the target portion at once; such an apparatus is commonly referred to as a wafer stepper.

In an alternative apparatus—commonly referred to as a step-and-scan apparatus—each target portion is irradiated by progressively scanning the mask pattern under the projection beam in a given reference direction (the "scanning" direction) while synchronously scanning the substrate table parallel or anti-parallel to this direction.

Regardless of the exact lithographic process used, the lithographically defined dimensions represent critical dimensions for the resultant devices, especially as the dimensions of devices are shrinking for increased integrations. As a consequence, it is important to not only ascertain the printed dimensions for quality assurance but also to use the dimensional information both in feed forward and feedback control. In feed forward control, other downstream processes are adjusted to account for any deviations in the lithographically printed dimensions (e.g., photoresist trim or metal line width etch). In feedback control, new wafers will be lithographically printed under conditions designed to compensate for any deviation from a target dimension. For example, the substrate to be processed may undergo various procedures such as priming, resist coating, and/or a soft bake where the recipes and conditions therein are adjusted to bring the lithographic printing to the target dimensions. Similarly, after exposure, the substrate may be subjected to other procedures such as a post-exposure bake (PEB), development and a hard bake, where conditions therein can likewise be adjusted.

Detailed Optical Tool Modeling

Conventional approaches to optical modeling of the hardware components have used a methodology based on numerical computation of the partial-derivatives of the ellipsometric quantities ψ and Δ with respect to the hardware parameters in order to capture the effect of systematic errors in the hardware. This being a numerical methodology, the results are limited by the particular hardware on which the derivatives are based and the particular sample that is modeled.

The invention endeavors to obtain analytical closed form expressions for the above derivatives which can then be used with any hardware measurement to reconstruct the measurements that would be obtained on an ideal hardware. In essence, this scheme maps the measurement from any particular hardware to corresponding measurements on the ideal hardware. The ideal hardware is characterized as an instrument with perfect components with perfectly known configuration parameters. On such an instrument, the measured (ψ, Δ) are exact and characterized only by the sample properties. Such a measurement is equivalent to (ψ, Δ) that is obtained by an accurate simulation that is based on the sample geometry and optical properties.

This is done by first measuring the error spectrum for a reference sample and then solving the inverse problem of deriving the systematic errors in the hardware from the obtained error spectrum. In the context of the invention, the inverse problem consists of solving for the error sources in the optical measurement tool, knowing the total error. For a completely characterized sample, the total error is the difference between the measured spectra and the theoretical true spectra. Given this circumstance, one needs to solve for the various error sources that contribute to the total error. For instance, the instrument may have certain azimuth errors and the polarizers in the instrument may be characterized by their attenuation coefficient. The total error introduced by these factors can be determined directly and the values for these sources need to be solved for, which constitutes the inverse problem. Solving the inverse problem can be accomplished using for example regression analysis, where for example analytical expressions for the total error from the optical instrument are used to develop data sets of the optical error vs. the error for each of the optical components, and regression used to determine a particular instrument error based on the measured total error.

The forward problem to determine the total error involves modeling an ellipsometer to predict the errors generated by each error source. The total predicted error is given by:

$$Err_{predicted} = \sum_i err(\Delta P_i)$$

where $\Delta P_i$ are the error sources in the hardware parameters that characterize a particular hardware.

To solve for $\Delta P_i$ (inverse problem) the following quantity should be minimized by regression:

$\Sigma(\text{Err}_{predicted} - \text{Err}_{measured})^2$ where the summation is over all the wavelengths.

Once the $\Delta P_i$ values are obtained as outlined above, these are associated with the particular hardware that was used for the reference measurement.

The optical measurements are, through application of the adaptive filter, mapped in comparison to the ideal hardware. This procedure is done by applying first-order corrections to the measured spectra. The first-order corrections are calculated as:

$$\Delta\psi = \sum_i \frac{\partial \psi}{\partial P_i} \Delta P_i$$

$$\Delta\Delta = \sum_i \frac{\partial \Delta}{\partial P_i} \Delta P_i$$

In one formalism, the Jacobian for $\psi$ and $\Delta$ are derived from modeling of the ellipsometer, as detailed below. A Jacobian as used here is a matrix of all first-order partial derivatives of a vector-valued function. A Jacobian typically represents the best linear approximation to a differentiable function near a given point. A Jacobian determinant at a given point p gives important information about the behavior of a function F near that point. For instance, a continuously differentiable function F is invertible near p if the Jacobian determinant at p is non-zero.

Rotating Analyzer Ellipsometer (RAE)

Figure 7:
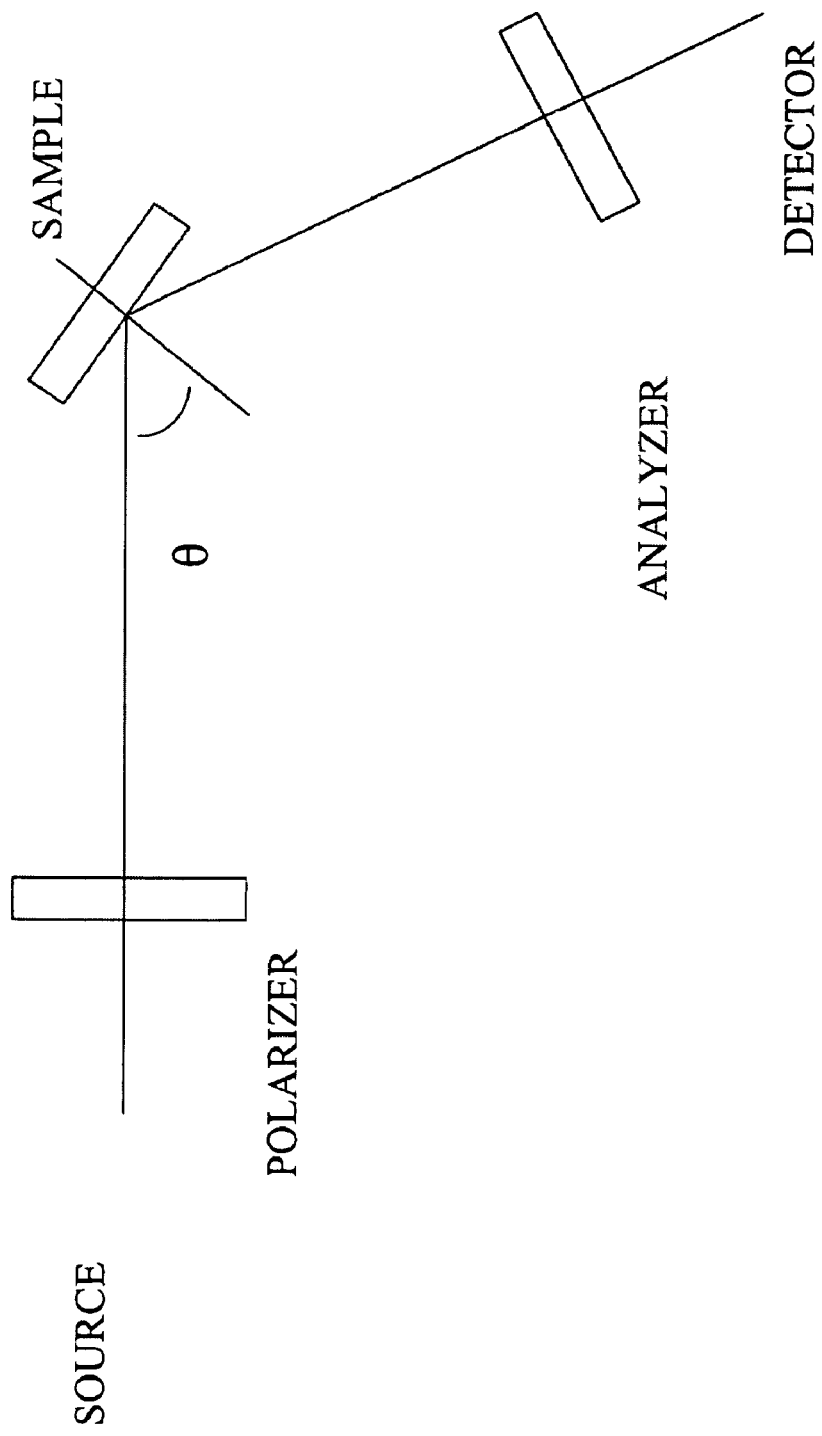
FIG. 7 is a schematic diagram of a rotating analyzer elllipsometer.

A model for an ellipsometer was established in order to derive the Jacobian for the ellipsometric parameters as well as to be able to solve the inverse problem described earlier. The Mueller-Stokes formalism was chosen to be used in the model since the Stokes parameters are ideal to represent both completely polarized light and partially polarized light. The Mueller matrices for different components of an ellipsometer are given in Table 1 included in FIG. 6. The basic configuration of an RAE is illustrated in FIG. 7.

The Stokes vector at the detector is given by $$S_D = R(-A) \cdot M_A \cdot R(A) \cdot M_{\omega,\Delta} \cdot R(-P) \cdot M_P \cdot R(P) \cdot S_0 \quad (0.1)$$

Since the incident light is unpolarized and the detector measures only the intensity of the reflected light, the rotation matrices at the extreme left and extreme right can be taken out. This yields $$S_D = M_A \cdot R(A) \cdot M_{\psi,\Delta} \cdot R(-P) \cdot M_P \cdot S_0 \quad (0.2)$$

The Ideal Rotating Analyzer Ellipsometer (RAE)

For a perfect RAE, the intensity at the detector evaluates to $$I_D = I_0 g(1 + \alpha \cos 2A + b \sin 2A) \quad (0.0.3)$$

where a and b, the normalized Fourier coefficients are $$a = \frac{\cos 2P - \cos 2\psi}{1 - \cos 2P \cos 2\psi} \quad (0.0.4)$$

$$b = \frac{\cos\Delta \sin 2\psi \sin 2P}{1 - \cos 2P \cos 2\psi}$$

$$g = 1 - \cos 2P \cos 2\psi$$

The ellipsometric quantities can be expressed in terms of the Fourier coefficients as $$\cos 2\psi = \frac{\cos 2P - a}{1 - a\cos 2P} \quad (0.0.5)$$

$$\cos\Delta = \frac{b}{\sqrt{1-a^2}}$$

Azimuth Errors

For an error dP in polarizer azimuth, the relevant expressions can be obtained by substituting P+dP in the expressions for the ideal RAE. The Jacobian with respect to the polarizer azimuth can also be derived by taking partial derivatives of the expressions for $\psi$ and $\Delta$ for the ideal RAE. If a different origin is chosen that is rotated through C from the original origin, the Fourier coefficients transform as follows $$a' = a \cos 2C + b \sin 2C$$

$$b' = -a \sin 2C + b \cos 2^C \quad (0.0.6)$$

the derivatives of the Fourier coefficients with respect to dA can be derived and multiplied with the derivatives of $\psi$ and $\Delta$ with respect to Fourier coefficients to yield the required Jacobian with respect to dA.

Depolarization

By inserting the Mueller matrix associated with a depolarizing component after the sample, the intensity at the detector is evaluated as:

$$I_D = I_0 g(1 + a' \cos 2A + b' \sin 2A)$$

where a' and b' are given by $$a' = \beta \frac{\cos 2P - \cos 2\psi}{1 - \cos 2P \cos 2\psi} \quad (0.0.7)$$

$$b' = \beta \frac{\cos\Delta \sin 2\psi \sin 2P}{1 - \cos 2P \cos 2\psi}$$

and $$\cos 2\psi = \frac{\beta \cos 2P - a'}{\beta - a' \cos 2P} \quad (0.0.8)$$

$$\cos\Delta = \frac{b'}{\sqrt{\beta^2 - a'^2}}$$

Defining $D = 1 - \beta$, the Jacobian with respect to dD is derivable from the above expressions. For an ideal RAE, $D = 0$.

Imperfect Components

For a polarizer with attenuation coefficient $\alpha_P$, the corresponding Mueller matrix is used, and the expressions evaluate to $$a' = \frac{(1-\alpha_p)\cos 2P - (1+\alpha_p)\cos 2\psi}{(1+\alpha_p) - (1-\alpha_p)\cos 2P \cos 2\psi} \quad (0.0.9)$$

$$b' = \frac{(1-\alpha_p)\cos\Delta \sin 2\psi \sin 2P}{(1+\alpha_p) - (1-\alpha_p)\cos 2P \cos 2\psi}$$

-continued $$\cos 2\psi = \frac{(1-\alpha_p)\cos 2P - a'(1+\alpha_p)}{(1+\alpha_p) - a'(1-\alpha_p)\cos 2P} \quad (0.0.10)$$

$$\cos\Delta = \frac{b'}{\sqrt{1-a'^2}} \frac{\sqrt{(1+\alpha_p)^2 - (1-\alpha_p)^2\cos^2 2P}}{(1-\alpha_p)\sin 2P}$$

From these the Jacobian with respect to $\alpha_p$ can be derived. Proceeding similarly for the analyzer with an attenuation coefficient $\alpha_a$, the expressions obtained are $$a' = \frac{(1-\alpha_a)(\cos 2P - \cos 2\psi)}{(1+\alpha_a)(1-\cos 2P\cos 2\psi)} \quad (0.0.11)$$

$$b' = \frac{(1-\alpha_a)\cos\Delta\sin 2\psi\sin 2P}{(1+\alpha_a)(1-\cos 2P\cos 2\psi)}$$

$$\cos 2\psi = \frac{(1-\alpha_a)\cos 2P - (1+\alpha_a)a'}{(1-\alpha_a) - a'(1+\alpha_a)\cos 2P} \quad (0.0.12)$$

$$\cos\Delta = \frac{b'(1+\alpha_a)}{\sqrt{(1-\alpha_a)^2 - a'^2(1+\alpha_a)^2}}$$

The Jacobian with respect to $\alpha_a$ can be derived from the above expressions. See Table 2 in FIG. 8 for detailed expressions of the Jacobian terms.

Rotating Compensator Ellipsometer

Figure 9:
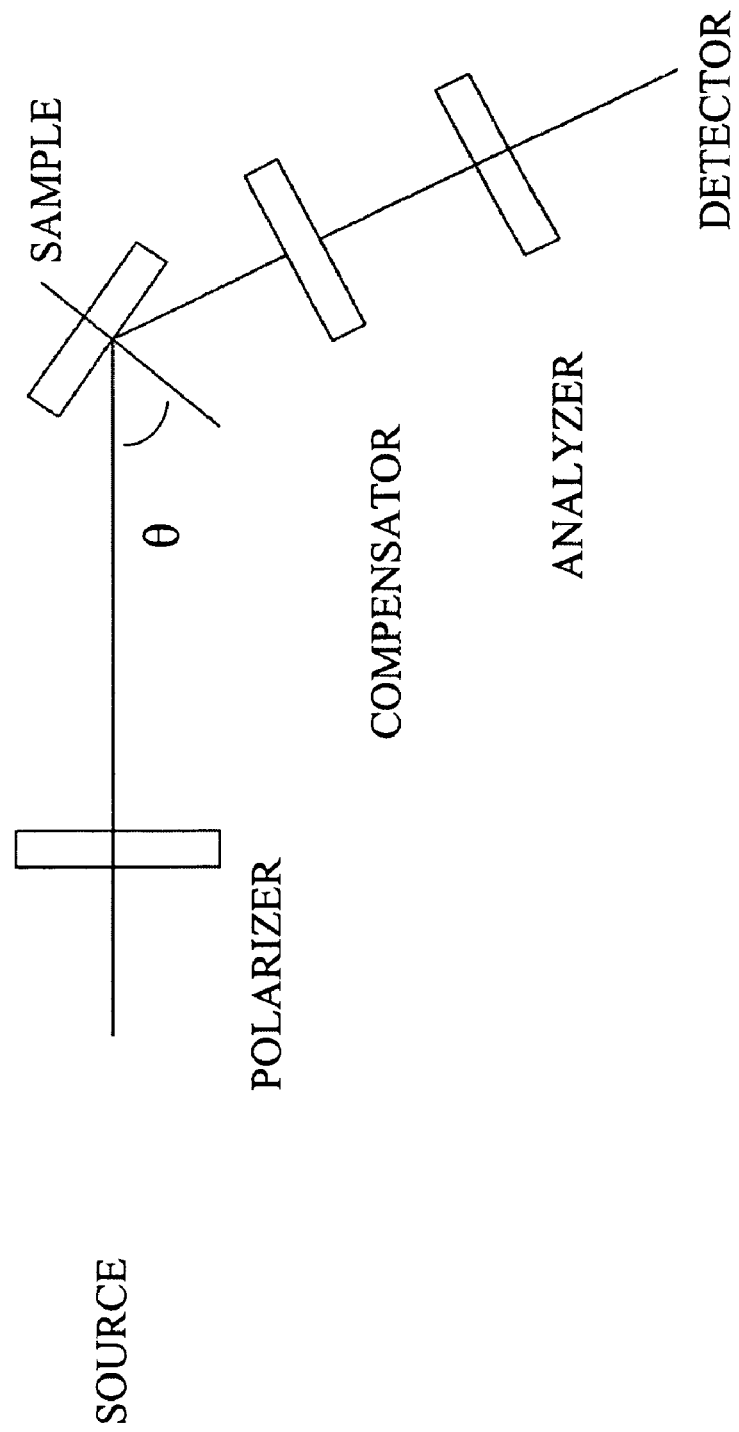
FIG. 9 is a schematic diagram of a rotating compensating polarizer analyzer elllipsometer.

One of the basic configurations of a rotating compensator ellipsometer RCE is illustrated in FIG. 9. Alternatively, PCSA configuration is also used in which the compensator is placed after the polarizer, before the sample. Using the Mueller formalism outlined in the previous chapter and the Mueller matrices given in Table 2, the intensity measured by an RCE device is given by $$I_D = A_0 + A_2 \cos 2C + B_2 \sin 2C + A_4 \cos 4C + B_4 \sin 4C,$$

where $A_0 = 1 - \cos 2P \cos 2\Psi + \frac{1}{2}(1+y_c)[\cos 2A(\cos 2P - \cos 2\Psi)$ $+ \sin 2A \sin 2P \sin 2\Psi \cos \Delta]$ $A_2 = x_c(\cos 2P - \cos 2\Psi)$ $+ x_c \cos 2A(1 - \cos 2P \cos 2\Psi) - z_c \sin 2A \sin 2P \sin 2\Psi \sin \Delta$ $B_2 = x_c \sin 2P \sin 2\Psi \cos \Delta$ $+ z_c \cos 2A \sin 2P \sin 2\Psi \sin \Delta + x_c \sin 2A(1 - \cos 2P \cos 2\Psi)$ $A_4 = \frac{1}{2}(1-y_c)[\cos 2A(\cos 2P - \cos 2\Psi) - \sin 2A \sin 2P \sin 2\Psi \cos \Delta]$ $B_4 = \frac{1}{2}(1-y_c)[\cos 2A \sin 2P \sin 2\Psi \cos \Delta + \sin 2A(\cos 2P - \cos 2\Psi)]$ (0.13)

Here the quantities $x_c$, $y_c$, and $z_c$ are given by $x_c \equiv \cos 2\Psi_c \approx 0$ $y_c \equiv \sin 2\Psi_c \cos \Delta_c \approx 0$ $z_c \equiv \sin 2\Psi_c \sin \Delta_c \approx 1$ (0.14)

The approximations shown above are accurate for an ideal compensator, i.e., $\Psi_c = 45°$ and $\Delta_c = 90°$ For P=45° and A=0°, which is a common setting in a RCE, the expressions for the Fourier coefficients simplify considerably $A_0 = 1 - \frac{1}{2}(1+y_c)\cos 2\Psi$ $A_2 = x_c(1 - \cos 2\Psi)$ $B_2 = x_c \sin 2\Psi \cos \Delta + z_c \sin 2\Psi \sin \Delta$ $A_4 = -\frac{1}{2}(1-y_c)\cos 2\Psi$ $B_4 = \frac{1}{2}(1-y_c)\sin 2\Psi \cos \Delta$ From these $\Psi, \Delta$ can be solved for. However, the coefficients $A_0$, $A_2$ are prone to error. Hence only $B_2$, $A_4$, $B_4$ are used. $B_2$, $B_4$ are normalized by scaling with $A_4$ $$\frac{B_2}{A_4} = -\frac{2x_c}{1-y_c}\tan 2\Psi \cos\Delta - \frac{2z_c}{1-y_c}\tan 2\Psi \sin\Delta$$

$$\frac{B_4}{A_4} = -\tan 2\Psi \cos\Delta$$

To simplify the final expression for the ellipsometric quantities, two intermediate quantities are introduced $$X_1 \equiv \tan 2\Psi \sin\Delta = \frac{x_c}{z_c}\frac{B_4}{A_4} - \frac{1-y_c}{2z_c}\frac{B_2}{A_4}$$

$$X_2 \equiv \tan 2\Psi \cos\Delta = -\frac{B_4}{A_4}$$

These can now be solved to give $$\tan 2\Psi = \sqrt{X_1^2 + X_2^2}$$

$$\tan\Delta = \frac{X_1}{X_2}$$

The exact values of $\Psi, \Delta$ can be established using sign information from the Fourier coefficients. Note that RCE can determine $\Delta$ exactly in the range 0-2π, unlike RAE which can only determine $\Delta$ in the range 0-π.

Polarizer Imperfection

For polarizer attenuation coefficient $\alpha_p$, the RCE Fourier coefficients are given by $$A_0 = (1+\alpha_p) - (1-\alpha_p)\cos 2P\cos 2\Psi + \quad (0.0.15)$$

$$\frac{1+y_c}{2}\{(1-\alpha_p)\sin 2A\sin 2P\sin 2\Psi\cos\Delta +$$

$$\cos 2A((1-\alpha_p)\cos 2P - (1+\alpha_p)\cos 2\Psi\}$$

$$A_2 = x_c((1-\alpha_p)\cos 2P - (1+\alpha_p)\cos 2\Psi) +$$

$$x_c \cos 2A((1+\alpha_p) - (1-\alpha_p)\cos 2P\cos 2\Psi) -$$

$$z_c(1-\alpha_p)\sin 2P\sin 2A\sin 2\Psi\sin\Delta$$

$$B_2 = x_c(1-\alpha_p)\sin 2P\sin 2\Psi\cos\Delta +$$

$$x_c((1+\alpha_p) - (1-\alpha_p)\sin 2A\cos 2P\cos 2\Psi) +$$

$$z_c(1-\alpha_p)\cos 2A\sin 2P\sin 2\Psi\sin\Delta$$

$$A_4 = \frac{(1-y_c)}{2}\{\cos 2A((1-\alpha_p)\cos 2P - (1+\alpha_p)\cos 2\Psi) -$$
$$(1-\alpha_p)\sin 2A\sin 2P\sin 2\Psi\cos\Delta\}$$

$$B_4 = \frac{(1-y_c)}{2}\{\sin 2A((1-\alpha_p)\cos 2P - (1+\alpha_p)\cos 2\Psi) +$$
$$(1-\alpha_p)\cos 2A\sin 2P\sin 2\Psi\cos\Delta\}$$

Analyzer Imperfection

For analyzer attenuation coefficient $\alpha_a$, the RCE Fourier coefficients are given by $$A_0 = (1+\alpha_a) - (1-\cos 2P\cos 2\Psi) + \frac{1+y_c}{2}(1- \tag{0.0.16}$$
$$\alpha_a)\{\sin 2A\sin 2P\sin 2\Psi\cos\Delta + \cos 2A(\cos 2P - \cos 2\Psi\}$$
$$A_2 = x_c(1-\alpha_a)(\cos 2P - \cos 2\Psi) +$$
$$x_c(1-\alpha_a)\cos 2A(1-\cos 2P\cos 2\Psi) -$$
$$z_c(1-\alpha_p)\sin 2P\sin 2A\sin 2\Psi\sin\Delta$$
$$B_2 = x_c(1+\alpha_a)\sin 2P\sin 2\Psi\cos\Delta +$$
$$x_c(1-\alpha_a)\sin 2A(1-\cos 2P\cos 2\Psi) +$$
$$z_c(1-\alpha_p)\cos 2A\sin 2P\sin 2\Psi\sin\Delta$$
$$A_4 = \frac{(1-y_c)}{2}(1-\alpha_a)\{(\cos 2A(\cos 2P - \cos 2\Psi) -$$
$$\sin 2A\sin 2P\sin 2\Psi\cos\Delta\}$$
$$B_4 = \frac{(1-y_c)}{2}(1-\alpha_a)\{\sin 2A(\cos 2P - \cos 2\Psi) +$$
$$\cos 2A\sin 2P\sin 2\Psi\cos\Delta\}$$

Polarizer and Analyzer Imperfection

If both components are imperfect, the Fourier coefficients are given by $$A_n = (1+\alpha_a)((1+\alpha_p) - (1-\alpha_p)\cos 2P\cos 2\Psi) + \tag{0.0.17}$$
$$\frac{1+y}{2}(1-\alpha_a)\{(1-\alpha_p)\sin 2A\sin 2P\sin 2\Psi\cos\Delta +$$
$$\cos 2A((1-\alpha_p)\cos 2P - (1+\alpha_p)\cos 2\Psi)\}$$
$$A_2 = x_c(1+\alpha_p)((1-\alpha)\cos 2P - (1+\alpha)\cos 2\Psi) +$$
$$x(1-\alpha_p)\cos 2A((1+\alpha_p) - (1-\alpha_p)\cos 2P\cos 2\Psi) -$$
$$z(1-\alpha_p)(1-\alpha_p)\sin 2P\sin 2A\sin 2\Psi\sin\Delta$$
$$B_2 = x_c(1+\alpha_p)(1-\alpha_p)\sin 2P\sin 2\Psi\cos\Delta +$$
$$x_c(1-\alpha_p)\sin 2A((1+\alpha_p) - (1-\alpha_p)\cos 2P\cos 2\Psi) +$$
$$z_c(1-\alpha_p)(1-\alpha_p)\cos 2A\sin 2P\sin 2\Psi\sin\Delta$$
$$A_4 = \frac{(1-y_c)}{2}(1-\alpha_a)\{\cos 2A((1-\alpha_p)\cos 2P - (1+\alpha_p)\cos 2\Psi) -$$
$$(1-\alpha_p)\sin 2A\sin 2P\sin 2\Psi\cos\Delta\}$$
$$B_4 = \frac{(1-y_c)}{2}(1-\alpha_a)\{\sin 2A((1-\alpha_p)\cos 2P - (1+\alpha_p)\cos 2\Psi) +$$
$$(1-\alpha_p)\cos 2A\sin 2P\sin 2\Psi\cos\Delta\}$$

For the common RCE settings of P=45°, A=0°, the first derivatives are summarized in Table 3 in FIG. 10.

Depolarization Due to NA

In an ellipsometer, due to the numerical aperture (NA) of the focusing optics, the light incident on the sample does not have a unique angle and plane of incidence. This results in different polarization state for each reflected ray in the reflected beam. As a consequence, the resulting beam is depolarized, thereby causing errors in the measurement.

The NA of the focusing lens in ellipsometers is usually very small, of the order of 0.1 or less.

Consider two plane waves with distinct polarization states. The electric fields are represented by $$\vec{R}_1 = R_{s1}e^{j\phi_{s1}}\hat{s} + R_{p1}e^{j\phi_{p1}}\hat{p} \tag{1.0.1}$$

$$\vec{R}_2 = R_{s2}e^{j\phi_{s2}}\hat{s} + R_{p2}e^{j\phi_{p2}}\hat{p} \tag{1.0.2}$$

Stokes vectors are given by $$\begin{bmatrix} S_{01} \\ S_{11} \\ S_{21} \\ S_{31} \end{bmatrix} = \begin{bmatrix} R_{s1}^2 + R_{p1}^2 \\ R_{s1}^2 - R_{p1}^2 \\ 2R_{s1}R_{p1}\cos\phi_1 \\ -2R_{s1}R_{p1}\sin\phi_1 \end{bmatrix} \tag{1.0.3}$$

$$\begin{bmatrix} S_{02} \\ S_{12} \\ S_{22} \\ S_{32} \end{bmatrix} = \begin{bmatrix} R_{s2}^2 + R_{p2}^2 \\ R_{s2}^2 - R_{p2}^2 \\ 2R_{s2}R_{p2}\cos\phi_2 \\ -2R_{s2}R_{p2}\sin\phi_2 \end{bmatrix} \tag{1.0.4}$$

where $\phi_1 = \phi_{s1} - \phi_{p1}$ and $\phi_2 = \phi_{s2} - \phi_{p2}$

The Stokes vector of the superposed wave is given by the sum of the 2 Stokes vectors.

$$\begin{bmatrix} S_0 \\ S_1 \\ S_2 \\ S_3 \end{bmatrix} = \begin{bmatrix} R_{s1}^2 + R_{p1}^2 + R_{s2}^2 + R_{p2}^2 \\ R_{s1}^2 - R_{p1}^2 + R_{s2}^2 - R_{p2}^2 \\ 2(R_{s1}R_{p1}\cos\phi_1 + R_{s2}R_{p2}\cos\phi_2) \\ -2(R_{s1}R_{p1}\sin\phi_1 + R_{s2}R_{p2}\sin\phi_2) \end{bmatrix} \tag{1.0.5}$$

Now, for the above vector $$S_1^2 + S_2^2 + S_3^2 = (R_{s1}^2 + R_{p1}^2)^2 + (R_{s2}^2 + R_{p2}^2)^2 + 2(R_{s1}^2 R_{s2}^2 + R_{p1}^2 R_{p2}^2 - R_{s1}^2 R_{p2}^2 - R_{s2}^2 R_{p1}^2) + 8R_{s1}R_{p1}R_{s2}R_{p2}\cos(\phi_1 - \phi_2) \tag{1.0.6}$$

$$S_0^2 = (R_{s1}^2 + R_{p1}^2)^2 + (R_{s2}^2 + R_{p2}^2)^2 + 2(R_{s1}^2 R_{s2}^2 + R_{p1}^2 R_{p2}^2 + R_{s1}^2 R_{p2}^2 + R_{s2}^2 R_{p1}^2) \tag{1.0.7}$$

The following comparison establishes when the result is physically meaningful:

$$S_0^2 \geq S_1^2 + S_2^2 + S_3^2 \Rightarrow 2(R_{s1}^2 R_{p2}^2 + R_{s2}^2 R_{p1}^2)$$
$$\geq 8R_{s1}R_{p1}R_{s2}R_{p2}\cos(\phi_1 - \phi_2) - 2(R_{s1}^2 R_{p2}^2 + R_{s2}^2 R_{p1}^2) \tag{1.0.8}$$

$$\Rightarrow (R_{s1}^2 R_{p2}^2 + R_{s2}^2 R_{p1}^2) \geq 2R_{s1}R_{p1}R_{s2}R_{p2}\cos(\phi_1 - \phi_2) \tag{1.0.9}$$

This is a valid inequality. Moreover, the equality is valid only when $R_{s1} = R_{s2}$, $R_{p1} = R_{p2}$ and $\phi_1 = \phi_2$, which is also meaningful since it implies that if the polarization states of the 2 beams are identical, the resulting beam has a degree of polarization (DOP) of 1.

Figure 11:
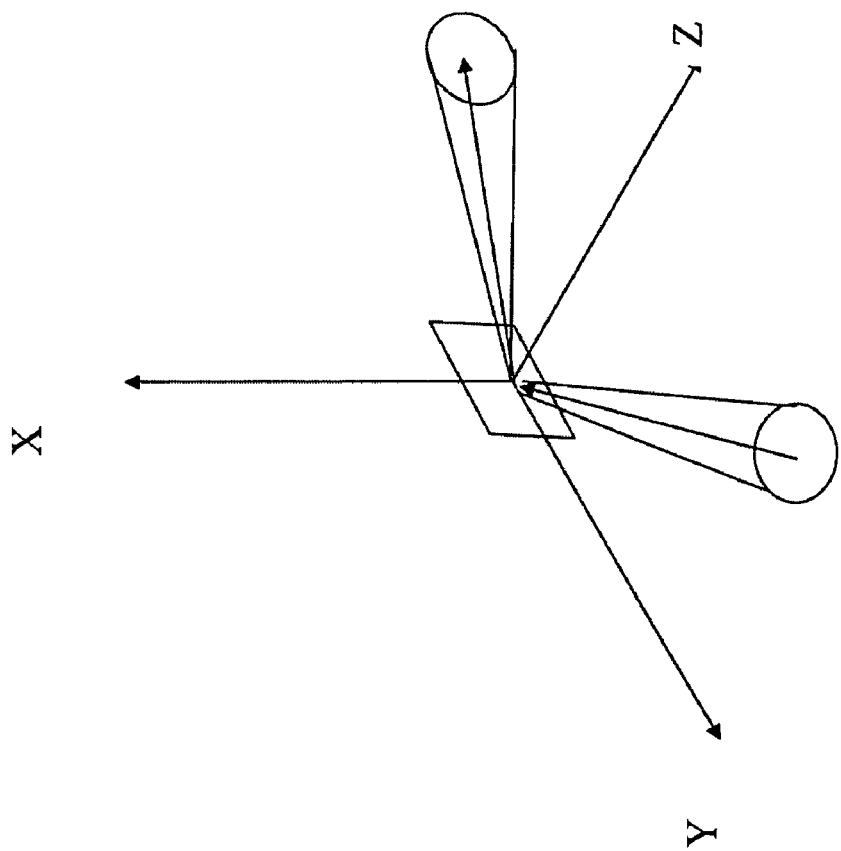
FIG. 11 is a schematic diagram of one modeling coordinate system.

This result indicates that, when waves of distinct polarization states are superposed, the resulting wave has a DOP <1, i.e. depolarization occurs. In order to derive the expression for the angle of incidence of each incident ray in FIG. 11, the relationship between the various relevant coordinate systems are defined. The relevant coordinate frames are
1) The global frame in which the z axis is aligned to the normal to the reflecting surface.
2) The local incidence frames with z axis aligned to the incident wave vectors
3) The local reflection frames with z axis aligned to the reflected wave vectors.

Of the frames described by 2) and 3), one frame in each of these sets is prominent; the ones in which the plane of incidence contains the central incident and the corresponding reflected wave-vectors. In what follows,
1) is denoted as (x, y, z),
2) is denoted as (x (δ, φ), y (δ, φ), z (δ, φ)),
3) is denoted as ($x_r$ (δ, φ), $y_r$ (δ, φ), $z_r$ (δ, φ))

The specific frame of the centrally incident wave-vector is denoted as (x', y', z') and that of the centrally reflected wave-vector is denoted as ($x'_r$, $y'_r$, $z'_r$)

Figure 12:
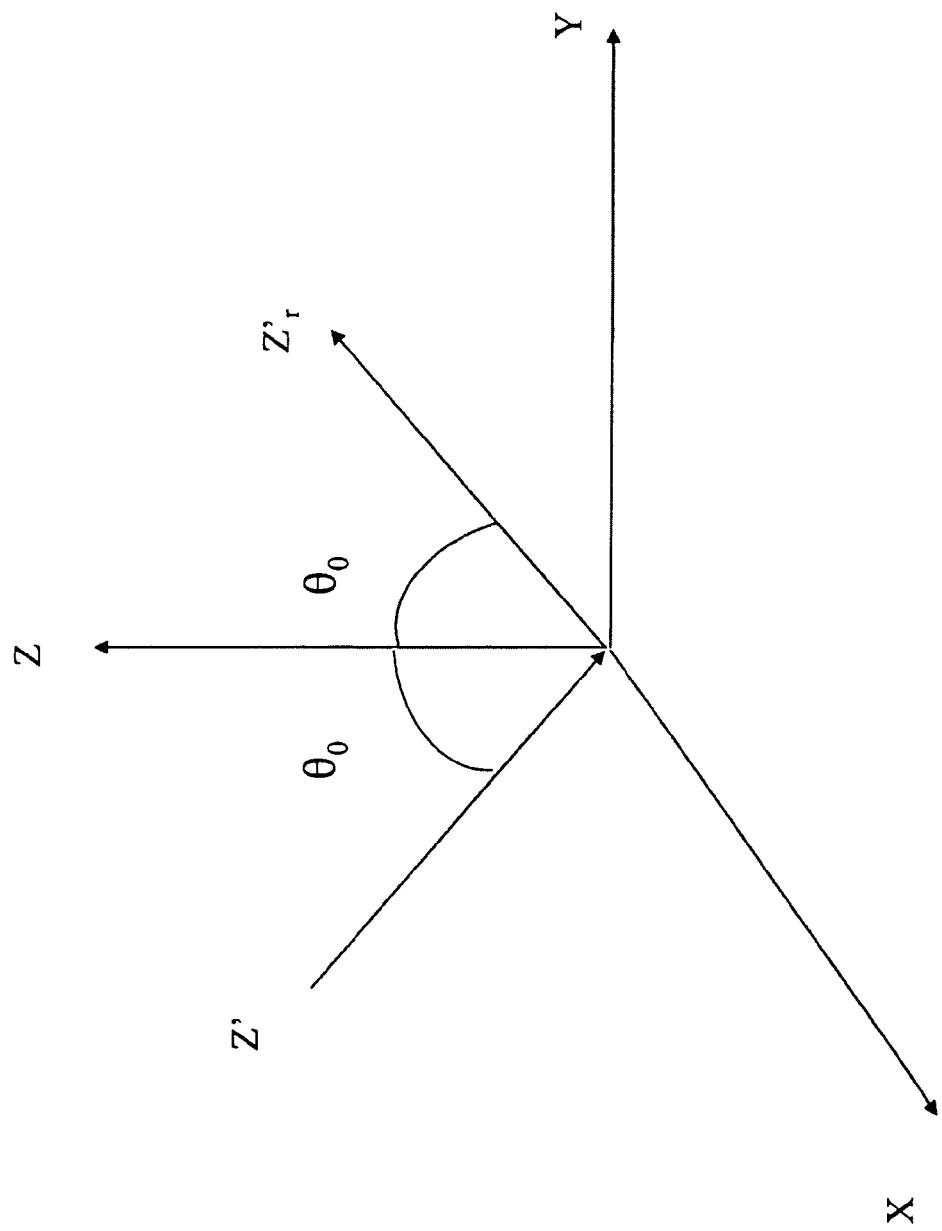
FIG. 12 is a schematic diagram of another modeling coordinate system.

For the global frame, x and y axes are chosen such that the plane of incidence of the central incident wave-vector lies in the yz plane. This is shown is FIG. 12, where the incident wave vectors are bunched in a cone around the central wave-vector and so are the corresponding reflected waves. The (x', y', z') axes and ($x'_r$, $y'_r$, $z'_r$) can be expressed in terms of (x, y, z). This is derived below.

$$\hat{z}' = -\cos\theta_0 \hat{z} + \sin\theta_0 \hat{y} \quad (1.2.1)$$

$$\hat{x}' = \frac{\hat{z}' \times \hat{z}}{|\hat{z}' \times \hat{z}|} = \hat{x}$$

$$\hat{y}' = \hat{z}' \times \hat{x}' = -\sin\theta_0 \hat{z} - \cos\theta_0 \hat{y}$$

This when inverted yields:

$$\hat{z} = -\cos\theta_0 \hat{z}' - \sin\theta_0 \hat{y}'$$

$$\hat{x} = \hat{x}'$$

$$\hat{y} = \hat{z} \times \hat{x} = \sin\theta_0 \hat{z}' - \cos\theta_0 \hat{y}' \quad (1.2.2)$$

Similarly, $$\hat{z}'_r = \cos\theta_0 \hat{z} + \sin\theta_0 \hat{y} \quad (1.2.3)$$

$$\hat{x}'_r = \frac{\hat{z}'_r \times \hat{z}}{|\hat{z}'_r \times \hat{z}|} = \hat{x}$$

$$\hat{y}'_r = \hat{z}'_r \times \hat{x}'_r = \sin\theta_0 \hat{z} - \cos\theta_0 \hat{y}$$

The above expression when inverted yields $$\hat{z} = \cos\theta_0 \hat{z}'_r - \sin\theta_0 \hat{y}'_r$$

$$\hat{x} = \hat{x}'_r$$

$$\hat{y} = \hat{z} \times \hat{x} = \sin\theta_0 \hat{z}'_r - \cos\theta_0 \hat{y}'_r \quad (1.2.4)$$

An arbitrary incident wave-vector can be expressed as $$\vec{k}(\delta,\phi) = k\hat{z}(\delta,\phi)$$

where $$\hat{z}(\delta,\phi) = \sin\delta\cos\phi\hat{x}' + \sin\delta\sin\phi\hat{y}' + \cos\delta\hat{z}' \quad (1.2.5)$$

$$\hat{x}(\delta, \varphi) = \frac{\hat{z}(\delta, \varphi) \times \hat{z}}{|\hat{z}(\delta, \varphi) \times \hat{z}|}$$

Using (1.2.5) and (1.2.2)

$$\hat{z}(\delta, \varphi) \times \hat{z} = \quad (1.2.6)$$

$$(\sin\delta\cos\varphi\hat{x}' + \sin\delta\sin\varphi\hat{y}' + \cos\delta\hat{z}') \times (-\cos\theta_0 \hat{z}' - \sin\theta_0 \hat{y}') =$$

$$\sin\delta\cos\varphi\cos\theta_0 \hat{y}' - \sin\delta\cos\varphi\sin\theta_0 \hat{z}' +$$

$$(\cos\delta\sin\theta_0 - \sin\delta\sin\varphi\cos\theta_0)\hat{x}'$$

$$|\hat{z}(\delta, \varphi) \times \hat{z}| = \sqrt{\sin^2\delta\cos^2\varphi + (\cos\delta\sin\theta_0 - \sin\delta\sin\varphi\cos\theta_0)^2}$$

For brevity, $$B = \cos\delta\sin\theta_0 - \sin\delta\sin\phi\cos\theta_0$$

$$C = \sin\delta\cos\phi \quad (1.2.7)$$

$$\hat{x}(\delta, \varphi) = \frac{B}{\sqrt{B^2 + C^2}}\hat{x}' + \frac{C\cos\theta_0}{\sqrt{B^2 + C^2}}\hat{y}' - \frac{C\sin\theta_0}{\sqrt{B^2 + C^2}}\hat{z}' \quad (1.2.8)$$

$$\hat{y}(\delta, \varphi) = \hat{z}(\delta, \varphi) \times \hat{x}(\delta, \varphi)$$

$$\frac{-AC}{\sqrt{B^2 + C^2}}\hat{x}' + \frac{B\cos\delta + C^2\sin\theta_0}{\sqrt{B^2 + C^2}}\hat{y}' +$$

$$\frac{C^2\cos\theta_0 - B\sin\delta\sin\varphi}{\sqrt{B^2 + C^2}}\hat{z}'$$

where $$A = \cos\delta\cos\theta_0 + \sin\delta\sin\phi\sin\theta_0$$

Note that $$A^2 + B^2 + C^2 = 1$$

Substituting (1.2.1) into (1.2.5), (1.2.8) and (1.2.9) yields:

$$\hat{z}(\delta, \varphi) = C\hat{x} + B\hat{y} - A\hat{z} \quad (1.2.10)$$

$$\hat{y}(\delta, \varphi) =$$

$$-\frac{AC}{\sqrt{B^2 + C^2}}\hat{x} - \frac{AB}{\sqrt{B^2 + C^2}}\hat{y} - \sqrt{B^2 + C^2}\hat{z}$$

$$\hat{x}(\delta, \varphi) = \frac{B}{\sqrt{B^2 + C^2}}\hat{x} - \frac{C}{\sqrt{B^2 + C^2}}\hat{y}$$

The direction of reflection $\hat{z}_r(\delta,\phi)$ is obtained by flipping the sign of the z-component and $\hat{y}_r(\delta,\phi)$, $\hat{x}_r(\delta,\phi)$ are obtained by taking appropriate cross-products.

$$\hat{z}_r(\delta, \varphi) = C\hat{x} + B\hat{y} + A\hat{z} \quad (1.2.11)$$

$$\hat{y}_r(\delta, \varphi) = \frac{AC}{\sqrt{B^2 + C^2}}\hat{x} + \frac{AB}{\sqrt{B^2 + C^2}}\hat{y} - \sqrt{B^2 + C^2}\hat{z}$$

$$\hat{x}_r(\delta, \varphi) = \frac{B}{\sqrt{B^2 + C^2}}\hat{x} - \frac{C}{\sqrt{B^2 + C^2}}\hat{y}$$

Substituting (1.2.4) into (1.2.11)

$$\hat{z}_r(\delta,\phi)=\sin\delta\cos\phi\hat{x}'_r+\cos\delta\hat{z}'_r$$

$$\hat{x}_r(\delta, \varphi) = \frac{B}{\sqrt{B^2+C^2}}\hat{x}'_r - \frac{C\cos\theta_0}{\sqrt{B^2+C^2}}\hat{y}'_r - \frac{C\sin\theta_0}{\sqrt{B^2+C^2}}\hat{z}'_r \quad (1.2.12)$$

$$\hat{y}_r(\delta, \varphi) = \frac{AC}{\sqrt{B^2+C^2}}\hat{x}'_r +$$
$$\frac{AB\cos\theta_0 + (B^2+C^2)\sin\theta_0}{\sqrt{B^2+C^2}}\hat{y}'_r + \frac{AB\sin\theta_0 - (B^2+C^2)\cos\theta_0}{\sqrt{B^2+C^2}}\hat{z}'_r$$

As expected, the reflected wave-vectors are bunched in a cone around the central reflected wave vector. Also, the angle of incidence is determined for each wave-vector. Note that in the global coordinate system, an arbitrary incident wave-vector can be expressed as $$\vec{k}=k\sin\theta\cos\alpha\hat{x}+k\sin\theta\sin\alpha\hat{y}-k\cos\theta\hat{z} \quad (1.2.13)$$

where θ is the angle of incidence and α determines the plane of incidence.

Comparing (1.2.13) with the first expression of (1.2.10):

$$\sin\cos\alpha=C$$
$$\sin\theta\sin\alpha=B$$
$$\cos\theta=A \quad (1.2.14)$$

$$\Rightarrow$$

$$\sin\theta = \quad (1.2.15)$$
$$\sqrt{B^2+C^2} = \sqrt{(\cos\delta\sin\theta_0 - \sin\delta\sin\varphi\cos\theta_0)^2 + \sin^2\delta\cos^2\varphi}$$
$$\cos\theta = A = \cos\delta\cos\theta_0 + \sin\delta\sin\varphi\sin\theta_0$$

$$\sin\alpha = \quad (1.2.16)$$
$$\frac{B}{\sqrt{B^2+C^2}} = \frac{\cos\delta\sin\theta - \sin\delta\sin\varphi\cos\theta_0}{\sqrt{(\cos\delta\sin\theta_0 - \sin\delta\sin\varphi\cos\theta_0)^2 + \sin^2\delta\cos^2\varphi}}$$

$$\cos\alpha = \frac{C}{\sqrt{B^2+C^2}} =$$
$$\frac{\sin\delta\cos\varphi}{\sqrt{(\cos\delta\sin\theta_0 - \sin\delta\sin\varphi\cos\theta_0)^2 + \sin^2\delta\cos^2\varphi}}$$

Stokes Vector of the Reflected Beam

The incident electric field can be expressed as $$\vec{E}(\delta,\phi)=E_s e^{i\Phi_s}\hat{x}(\delta,\phi)+E_p e^{i\phi_p}\hat{y}(\delta,\phi) \quad (1.3.1)$$

The reflected field is given by $$\vec{R}(\delta,\phi)=R_s e^{i\Phi_s}\hat{x}_r(\delta,\phi)+R_p e^{i\phi_p}\hat{y}_r(\delta,\phi) \quad (1.3.2)$$

where $$R_s=r_s(\theta)E_s=r_s(\delta,\phi)E_s$$

$$R_p=r_p(\theta)E_p=r_p(\delta,\phi)E_p \quad (1.3.3)$$

$r_s$ and $r_p$ being the reflection coefficients of the sample.

The Stokes vector for each individual wave-vector can be constructed in the local reference frame of each vector. The Stokes vector for any given reflected wave follows:

$$S_0(\delta,\phi)=\cos\theta(R_s^2+R_p^2)$$
$$S_1(\delta,\phi)=\cos\theta(R_s^2-R_p^2)$$
$$S_3(\delta,\phi)=2\cos\theta R_s R_p\cos\phi$$
$$S_4(\delta,\phi)=2\cos\theta R_s R_p\sin\phi \quad (1.3.4)$$

where θ is the angle of incidence of the wave, φ is the phase difference between the orthogonal components of the electric field of the reflected wave.

To simplify (1.2.15) use the following.

Since δ<<1, use the following approximations to second order $$\cos\delta\approx -\delta^1/2$$
$$\sin\delta\approx\delta \quad (1.3.5)$$

The expression for cos θ follows from (1.2.15)

$$\cos\theta=\cos\delta\cos\theta_0+\sin\delta\sin\phi\sin\theta_0 \quad (1.3.6)$$

Applying the above approximations to (1.2.15)

$$\cos\theta\approx(1-\tfrac{1}{2}\delta^2)\cos\theta_0+\delta\sin\phi\sin\theta_0 \quad (1.3.7)$$

A Taylor expansion to $2^{nd}$ order of $r_s(\theta)$ and $r_p(\theta)$ around $\theta_0$ is equivalent to expanding around δ=0.

For an arbitrary sample, the reflection coefficients can be expressed as $$r_s(\delta, \varphi) \simeq r_s(\theta_0) + \delta r'_s(\theta_0)\frac{\partial\theta}{\partial\delta}\bigg|_{\delta=0} + \frac{\delta^2}{2}r''_s(\theta_0)\frac{\partial^2\theta}{\partial\delta^2}\bigg|_{\delta=0} \quad (1.3.8)$$

$$r_p(\delta, \varphi) \simeq r_p(\theta_0) + \delta r'_p(\theta_0)\frac{\partial\theta}{\partial\delta}\bigg|_{\delta=0} + \frac{\delta^2}{2}r''_p(\theta_0)\frac{\partial^2\theta}{\partial\delta^2}\bigg|_{\delta=0} \quad (1.3.9)$$

Taking derivative of (1.3.6):

$$-\sin\theta\frac{\partial\theta}{\partial\delta} = -\sin\delta\cos\theta_0 + \cos\delta\sin\varphi\sin\theta_0 \quad (1.3.10)$$

$$\Rightarrow \frac{\partial\theta}{\partial\delta}\bigg|_{\delta=0} = -\sin\varphi \quad (1.3.11)$$

Taking derivative of (1.3.10)

$$-\sin\theta\frac{\partial^2\theta}{\partial\delta^2} - \cos\theta\left(\frac{\partial\theta}{\partial\delta}\right)^2 = \quad (1.3.12)$$
$$-\cos\delta\cos\theta_0 - \sin\delta\sin\varphi\sin\theta_0 - \sin\theta\frac{\partial^2\theta}{\partial\delta^2} =$$
$$\cos\theta\left(\frac{\partial\theta}{\partial\delta}\right)^2 - \cos\delta\cos\theta_0 - \sin\delta\sin\varphi\sin\theta_0 \Rightarrow \frac{\partial^2\theta}{\partial\delta^2}\bigg|_{\delta=0} =$$
$$\cot\theta_0\cos^2\varphi$$

Substituting (1.3.11) and (1.3.12) into (1.3.8) and (1.3.9):

$$r_s(\delta, \varphi) \simeq r_s(\theta_0) - \delta\sin\varphi r'_s(\theta_0) + \frac{\delta^2}{2}\cot\theta_0\cos^2\varphi r''_s(\theta_0) \quad (1.3.13)$$

$$r_p(\delta, \varphi) \simeq r_p(\theta_0) - \delta\sin\varphi r'_p(\theta_0) + \frac{\delta^2}{2}\cot\theta_0\cos^2\varphi r''_p(\theta_0) \quad (1.3.14)$$

-continued $$r_s(\delta,\varphi)r_p(\delta,\varphi) \simeq r_s(\theta_0)r_p(\theta_0) - \quad (1.3.15)$$
$$\delta\sin\varphi(r'_p(\theta_0)r_s(\theta_0) + r'_s(\theta_0)r_p(\theta_0)) + \delta^2\Big(\sin^2\varphi r'_s(\theta_0)r'_p(\theta_0) +$$
$$\frac{1}{2}\cot\theta_0\cos^2\varphi(r''_p(\theta_0)r_s(\theta_0) + r''_s(\theta_0)r_p(\theta_0))\Big)$$

$$r_s^2(\delta,\varphi) \simeq r_s^2(\theta_0) - 2\delta\sin\varphi r'_s(\theta_0)r_s(\theta_0) + \quad (1.3.16)$$
$$\delta^2(\sin^2\varphi r'^2_s(\theta_0) + \cot\theta_0\cos^2\varphi r''_s(\theta_0)r_s(\theta_0))$$

$$r_p^2(\delta,\varphi) \simeq r_p^2(\theta_0) - 2\delta\sin\varphi r'_p(\theta_0)r_p(\theta_0) + \quad (1.3.17)$$
$$\delta^2(\sin^2\varphi r'^2_p(\theta_0) + \cot\theta_0\cos^2\varphi r''_p(\theta_0)r_p(\theta_0))$$

The Stokes vector for each individual wave-vector can now be constructed as follows $$S_0(\delta,\phi) = \cos\theta(R_s^2 + R_p^2) = \cos\theta r_s^2(\delta,\phi)E_s^2 + \cos\theta r_p^2(\delta,\phi)E_p^2)$$

$$S_1(\delta,\phi) = \cos\theta(R_s^2 - R_p^2) = \cos\theta r_s^2(\delta,\phi)E_s^2 - \cos\theta r_p^2(\delta,\phi)E_p^2)$$

$$S_3(\delta,\phi) = 2\cos\theta R_s R_p \cos\phi = 2\cos\theta r_s(\delta,\phi)r_p(\delta,\phi)E_s E_p \cos\phi$$

$$S_4(\delta,\phi) = 2\cos\theta R_s R_p \sin\phi = 2\cos\theta r_s(\delta,\phi)r_p(\delta,\phi)E_s E_p \sin\phi \quad (1.3.18)$$

To construct the Stokes vector as above, the following 3 terms are evaluated in terms of $\delta,\phi$ $$\cos\theta r_s^2(\delta,\phi)$$
$$\cos\theta r_p^2(\delta,\phi)$$
$$\cos\theta r_s(\delta,\phi)r_p(\delta,\phi)$$

The above terms can be evaluated using (1.3.7), (1.3.16), (1.3.17) and (1.3.15). This is derived in detail below $$\cos\theta r_s(\delta,\varphi)r_p(\delta,\varphi) \simeq \cos\theta_0 r_s(\theta_0)r_p(\theta_0) + \quad (1.3.19)$$
$$\frac{\delta^2}{2}\cos\theta_0(\cos^2\varphi\cot\theta_0(r''_p(\theta_0)r_s(\theta_0) + r''_s(\theta_0)r_p(\theta_0)) -$$
$$r_s(\theta_0)r_p(\theta_0)) + \delta\sin\varphi(\sin\theta_0 r_s(\theta_0)r_p(\theta_0) -$$
$$\cos\theta_0(r'_p(\theta_0)r_s(\theta_0) + r'_s(\theta_0)r_p(\theta_0))) +$$
$$\delta^2\sin^2\varphi(\cos\theta_0 r'_s(\theta_0)r'_p(\theta_0) -$$
$$\sin\theta_0(r'_p(\theta_0)r_s(\theta_0) + r'_s(\theta_0)r_p(\theta_0)))$$

$$\cos\theta r_s^2(\delta,\varphi) \simeq \cos\theta_0 r_s^2(\theta_0) + \quad (1.3.20)$$
$$\frac{\delta^2}{2}\cos\theta_0(2\cos^2\varphi\cot\theta_0 r''_s(\theta_0)r_s(\theta_0) - r_s^2(\theta_0)) +$$
$$\delta\sin\varphi(\sin\theta_0 r_s^2(\theta_0) - 2\cos\theta_0 r'_s(\theta_0)r_s(\theta_0)) +$$
$$\delta^2\sin^2\varphi(\cos\theta_0 r'^2_s(\theta_0) - 2\sin\theta_0 r'_s(\theta_0)r_s(\theta_0))$$

$$\cos\theta r_p^2(\delta,\varphi) \simeq \cos\theta_0 r_p^2(\theta_0) + \quad (1.3.21)$$
$$\frac{\delta^2}{2}\cos\theta_0(2\cos^2\varphi\cot\theta_0 r''_p(\theta_0)r_p(\theta_0) - r_p^2(\theta_0)) +$$
$$\delta\sin\varphi(\sin\theta_0 r_p^2(\theta_0) - 2\cos\theta_0 r'_p(\theta_0)r_p(\theta_0)) +$$
$$\delta^2\sin^2\varphi(\cos\theta_0 r'^2_p(\theta_0) - 2\sin\theta_0 r'_p(\theta_0)r_p(\theta_0))$$

Stokes Vector of Collimated Beam

To obtain a Stokes vector of the collimated beam, the Stokes vectors are summed over all the wave-vectors and normalized. This is given by $$S_0 = \int_0^{\delta_m}\int_0^{2\pi} S_0(\delta,\varphi)\sin\delta\,d\delta\,d\varphi \simeq \quad (1.4.1)$$
$$E_s^2\int_0^{\delta_m}\int_0^{2\pi}\cos\theta r_s^2\delta\,d\delta\,d\varphi + E_p^2\int_0^{\delta_m}\int_0^{2\pi}\cos\theta r_p^2\delta\,d\delta\,d\varphi$$

$$S_1 = \int_0^{\delta_m}\int_0^{2\pi} S_1(\delta,\varphi)\sin\delta\,d\delta\,d\varphi \simeq$$
$$E_s^2\int_0^{\delta_m}\int_0^{2\pi}\cos\theta r_s^2\delta\,d\delta\,d\varphi - E_p^2\int_0^{\delta_m}\int_0^{2\pi}\cos\theta r_p^2\delta\,d\delta\,d\varphi$$

$$S_2 = \int_0^{\delta_m}\int_0^{2\pi} S_2(\delta,\varphi)\sin\delta\,d\delta\,d\varphi \simeq$$
$$2E_s E_p\cos\phi\int_0^{\delta_m}\int_0^{2\pi}\cos\theta r_s r_p\delta\,d\delta\,d\varphi$$

$$S_3 = \int_0^{\delta_m}\int_0^{2\pi} S_3(\delta,\varphi)\sin\delta\,d\delta\,d\varphi \simeq$$
$$2E_s E_p\sin\phi\int_0^{\delta_m}\int_0^{2\pi}\cos\theta r_s r_p\delta\,d\delta\,d\varphi$$

The Stokes vector is normalized by dividing by the solid angle. The resulting vector can be expressed as $$S_0 = AE_s^2 + BE_p^2$$
$$S = AE_s^2 - BE_p^2$$
$$S_2 = 2CE_s E_p\cos\phi$$
$$S_3 = 2CE_s E_p\sin\phi \quad (1.4.2)$$

To evaluate A, B and C, the following integrals are evaluated $$\int_0^{\delta_m}\int_0^{2\pi}\delta\,d\delta\,d\varphi = \pi\delta_m^2 \quad (1.4.3)$$

$$\int_0^{\delta_m}\int_0^{2\pi}\delta^3\,d\delta\,d\varphi = \frac{\pi\delta_m^4}{2} \quad (1.4.4)$$

$$\int_0^{\delta_m}\int_0^{2\pi}\delta^2\,d\delta\sin\varphi\,d\varphi = \int_0^{\delta_m}\int_0^{2\pi}\delta^3\,d\delta\sin\varphi\,d\varphi = 0 \quad (1.4.5)$$

$$\int_0^{\delta_m}\int_0^{2\pi}\delta^3\,d\delta\sin^2\varphi\,d\varphi = \int_0^{\delta_m}\int_0^{2\pi}\delta^3\,d\delta\cos^2\varphi\,d\varphi = \frac{\pi\delta_m^4}{4} \quad (1.4.6)$$

A, B, C are evaluated as $$A = \frac{\int_0^{\delta_m}\int_0^{2\pi}\sin\delta\cos\theta r_s^2(\delta,\varphi)d\delta d\varphi}{\int_0^{\delta_m}\int_0^{2\pi}\sin\delta d\delta d\varphi} \simeq \cos\theta_0(r_s^2(\theta_0) + a\delta_m^2) \quad (1.4.7)$$

$$B = \frac{\int_0^{\delta_m}\int_0^{2\pi}\sin\delta\cos\theta r_p^2(\delta,\varphi)d\delta d\varphi}{\int_0^{\delta_m}\int_0^{2\pi}\sin\delta d\delta d\varphi} \simeq \cos\theta_0(r_p^2(\theta_0) + b\delta_m^2) \quad (1.4.8)$$

$$C = \frac{\int_0^{\delta_m}\int_0^{2\pi}\sin\delta\cos\theta r_s(\delta,\varphi)r_p(\delta,\varphi)d\delta d\varphi}{\int_0^{\delta_m}\int_0^{2\pi}\sin\delta d\delta d\varphi} \simeq \quad (1.4.9)$$

-continued $$\cos\theta_0(r_s(\theta_0)r_p(\theta) + c\delta_m^2)$$

where a, b, c are given by $$a = \frac{1}{4}[r_s'^2(\theta_0) - r_s^2(\theta_0) + \cot\theta_0 r_s(\theta_0)r_s''(\theta_0) - 2\tan\theta_0 r_s(\theta_0)r_s'(\theta_0)] \quad (1.4.10)$$

$$b = \frac{1}{4}[r_p'^2(\theta_0) - r_p^2(\theta_0) + \cot\theta_0 r_p(\theta_0)r_p''(\theta_0) - 2\tan\theta_0 r_p(\theta_0)r_p'(\theta_0)] \quad (1.4.11)$$

$$c = \frac{1}{4}\Big[r_s'(\theta_0)r_p'(\theta_0) - r_s(\theta_0)r_p(\theta_0) + \quad (1.4.12)$$
$$\frac{1}{2}\cot\theta_0(r_s(\theta_0)r_p''(\theta_0) + r_p(\theta_0)r_s''(\theta_0)) -$$
$$\tan\theta_0(r_s(\theta_0)r_p'(\theta_0) + r_p(\theta_0)r_s'(\theta_0))\Big]$$

Degree of Polarization (DOP) of Collimated Reflected Beam

From (1.4.2), the DOP is calculated as $$\beta^2 = \frac{S_1^2 + S_2^2 + S_3^2}{S_0^2} = \frac{(AE_s^2 - BE_p^2)^2 + 4C^2 E_s^2 E_p^2}{(AE_s^2 + BE_p^2)^2} \simeq \quad (1.5.1)$$

$$\frac{((r_s^2(\theta_0) + a\delta_m^2)E_s^2 - (r_p^2(\theta_0) + b\delta_m^2)E_p^2)^2 +}{((r_s^2(\theta_0) + a\delta_m^2)E_s^2 + (r_p^2(\theta_0) + b\delta_m^2)E_p^2)^2} \simeq$$
$$\frac{4(r_s(\theta_0)r_p(\theta_0) + c\delta_m^2)^2 E_s^2 E_p^2}{((r_s^2(\theta_0) + a\delta_m^2)E_s^2 + (r_p^2(\theta_0) + b\delta_m^2)E_p^2)^2}$$

$$\frac{(r_s^2(\theta_0)E_s^2 - r_p^2(\theta_0)E_p^2 + a\delta_m^2 E_s^2 - b\delta_m^2 E_p^2)^2 +}{(r_s^2(\theta_0)E_s^2 + r_p^2(\theta_0)E_p^2 + a\delta_m^2 E_s^2 + b\delta_m^2 E_p^2)^2} \simeq$$
$$\frac{4(r_s^2(\theta_0)r_p^2(\theta_0) + 2c\delta_m^2 r_s(\theta_0)r_p(\theta_0))E_s^2 E_p^2}{(r_s^2(\theta_0)E_s^2 + r_p^2(\theta_0)E_p^2 + a\delta_m^2 E_s^2 + b\delta_m^2 E_p^2)^2}$$

$$\frac{d^2 + 2\delta_m^2((aE_s^2 - bE_p^2)(r_s^2(\theta_0)E_s^2 - r_p^2(\theta_0)E_p^2) +}{d^2 + 2\delta_m^2(aE_s^2 + bE_p^2)(r_s^2(\theta_0)E_s^2 + r_p^2(\theta_0)E_p^2)} \simeq$$
$$\frac{4cr_s(\theta_0)r_p(\theta_0)E_s^2 E_p^2)}{}$$

$$\left(1 + \frac{2\delta_m^2}{d^2}((w-x)(y-z) + 4cr_s(\theta_0)r_p(\theta_0)E_s^2 E_p^2)\right)$$
$$\left(1 - \frac{2\delta_m^2}{d^2}(w+x)(y+z)\right) \simeq$$

$$1 + \frac{2\delta_m^2}{d^2}((w-x)(y-z) + 4cr_s(\theta_0)r_p(\theta_0)E_s^2 E_p^2) -$$
$$\frac{2\delta_m^2}{d^2}(w+x)(y+z) \simeq$$

$$1 + \frac{2\delta_m^2}{d^2}((w-x)(y-z) - (w+x)(y+z) + 4cr_s(\theta_0)r_p(\theta_0)E_s^2 E_p^2)$$

$$\simeq 1 - \frac{4\delta_m^2 E_s^2 E_p^2}{d^2}((ar_p^2(\theta_0) + br_s^2(\theta_0)) - 2cr_s(\theta_0)r_p(\theta_0)) \quad (1.5.2)$$

$$\beta \simeq 1 - \frac{2\delta_m^2 E_s^2 E_p^2}{d^2}((ar_p^2(\theta_0) + br_s^2(\theta_0)) - 2cr_s(\theta_0)r_p(\theta_0)) \quad (1.5.3)$$

$$\Rightarrow \beta \simeq 1 - \frac{\delta_m^2 E_s^2 E_p^2}{2} \frac{(r_s(\theta_0)r_p'(\theta_0) - r_p(\theta_0)r_s'(\theta_0))^2}{(r_s^2(\theta_0)E_s^2 + r_p^2(\theta_0)E_p^2)^2} \quad (1.5.4)$$

From the above expression, $\beta=1$, if either $E_s=0$ or $E_p=0$.

If $E_s=E_p$, (which is a very common case in ellipsometry), the expression reduces to $$\Rightarrow \beta \simeq 1 - \frac{\delta_m^2}{2} \frac{(r_s(\theta_0)r_p'(\theta_0) - r_p(\theta_0)r_s'(\theta_0))^2}{(r_s^2(\theta_0) + r_p^2(\theta_0))^2} \quad (1.5.5)$$

Modeling Results for Degree of Polarization Effects

The DOP in the optical metrology tool can be numerically evaluated without using any approximations. As noted above, the hardware error $\Delta P_i$ is predicated on the calculation of the "ideal" spectrum for a reference sample based on modeling of the optical metrology tool. Heretofore, efforts to model and then utilize the model for the optical metrology tools of interest here had been frustrated by the lack closed form analytical solution for tool error such as the degree of polarization. Without a closed form analytical solution, one would have to rely on either time intensive numerical convergence solutions which would frustrate utilization in a manufacturing line where real time solutions are needed or would have to rely on approximation solutions. However, using approximation solutions introduces error which is self-defeating when one is attempting to remove hardware error in order to make a better determination of the optical structure.

The approach here for the first time is based on a theoretical framework, relying on experimental measurement only for purposes of validation. Development of the hardware errors $\Delta P_i$ was approached from the ground up by first gaining an understanding of the errors in the measurement produced by any particular hardware and the sources of such errors. These are the systematic errors inherent in a particular hardware that occur due to errors in the hardware settings and imperfections in the hardware components.

Expressions have been obtained for the following error sources: 1) component azimuth errors, 2) component imperfections, and 3) error due to depolarization of light incident on the detector.

Of the above, azimuth errors and component imperfection are inherent to the optical metrology device used for the measurement and are not sample dependent. Depolarization, however, is typically caused by the reflection properties of the sample and is therefore sample dependent. The common sources of depolarization of the reflected light are spread of incident angle, thickness variation across sample surface, variation of optical constants across sample surface and incoherent superposition of light reflected from different layers of the sample.

Modeling based on the analytic expressions that were developed, indicates that errors introduced in the ellipsometric quantities due to polarizer/analyzer imperfection and depolarization need to be accounted for. Also, depolarization and polarizer/analyzer imperfection are wavelength dependent and hence cannot be directly determined by solving the inverse problem of determining error sources from the total measured error spectrum.

From our study of depolarization resulting from the spread in angle of incidence, caused by the numerical aperture of the focusing optics, a closed-form analytic expression has been obtained that quantifies the depolarization caused due to small numerical aperture NA. To the inventor's knowledge, no prior work analytically quantifies this source of depolarization.

The expression for the Degree Of Polarization (DOP) of the reflected light is presented below.

$$\beta \simeq 1 - \frac{\delta_m^2 E_s^2 E_p^2}{2} \frac{(r_s(\theta_0) r'_p(\theta_0) - r_p(\theta_0) r'_s(\theta_0))^2}{(r_s^2(\theta_0) E_s^2 + r_p^2(\theta_0) E_p^2)^2}$$

Where $\delta_m$ is the NA of the focusing optics of the device and $r_s$ and $r_p$ are the reflection coefficients of the reflecting sample, $\theta_0$ is the Angle Of Incidence (AOI), $E_s$ and $E_p$ are the components of the incident field amplitude. Analytic expressions for predicting polarizer/analyzer imperfection for wire-grid based components, given the grid parameters, were obtained, making possible a methodology for realizing the hardware errors.

A given hardware is characterized by the errors inherent in the hardware. This is done by solving the inverse problem of determining the error sources in the hardware by measuring the total error that is caused in the measurement done on the reference sample for which the "ideal" measurement is known (as discussed above).

This hardware characterization yields the azimuth errors and the component imperfections inherent in the hardware. However, the depolarization that is obtained by solving the inverse-problem is specific to the reference sample on which the measurement was carried out. The following is a suitable strategy according to one embodiment of the invention which applies the overall correction for the measurement obtained for any sample on the hardware.

The correction for hardware specific errors is applied. This partially corrected measurement is then analyzed by the library matching software and a match is obtained. Using the model obtained from the match, depolarization is computed given the NA of the hardware. The correction of this is then applied and is again analyzed by the software for a match. This process is carried out iteratively until an appropriate exit condition is met. This process was referred to above as the iterative approach.

Indeed, sensitivity analysis indicated that depolarization and polarizer/analyzer imperfection were potentially dominant sources of errors in ellipsometric measurements. Since both of these factors are wavelength dependent, these factors were modeled in order to be able to solve the inverse problem of determining error sources from the measured error spectrum.

Application and Solution for a Rotating Analyzer Ellipsometer

In particular, the present inventors have used the above-noted theoretical framework to develop a closed analytical solution for a rotating analyzer ellipsometer RAE, whose details are provided below.

The spectra of a particular sample yield different Fourier coefficients on different RAE devices (using the same hardware parameter settings) based on the relevant hardware imperfections. The imperfections inherent in a hardware RAE device were characterized by the following set of parameters: dP, dA, $\alpha_p$, $\alpha_a$, NA which stand for the polarizer azimuth error, analyzer azimuth error, polarizer attenuation coefficient, analyzer attenuation coefficient and Numerical Aperture respectively. The measured Fourier coefficients in the case of dA=0, is related to as follows $$a' = \beta \alpha'_a \frac{\alpha'_p \cos 2P' - \cos 2\Psi}{1 - \alpha'_p \cos 2P' \cos 2\Psi} \quad (1.1)$$

-continued
$$b' = \beta \alpha'_a \frac{\alpha'_p \sin 2P' \cos \Delta \sin 2\Psi}{1 - \alpha'_p \cos 2P' \cos 2\Psi}$$

where $$\alpha'_p = \frac{1 - \alpha_p}{1 + \alpha_p}$$

$$\alpha'_a = \frac{1 - \alpha_a}{1 + \alpha_a}$$

$$P' = P + dP$$

$$\alpha = f(NA)$$

For dA$\neq$0, the Fourier coefficients are given by $$a = a' \cos 2dA + b' \sin 2dA$$

$$b = b' \cos 2dA - a' \sin 2dA \quad (1.2)$$

Equation (1.1) is more compactly expressed as $$a'' = \frac{C2P - \cos 2\Psi}{1 - C2P \cos 2\Psi} \quad (1.3)$$

$$b'' = \frac{S2P \cos \Delta \sin 2\Psi}{1 - C2P \cos 2\Psi}$$

where $$a'' = \frac{a'}{\beta \alpha'_a}$$

$$b'' = \frac{b'}{\beta \alpha'_a}$$

$$C2P = \alpha'_p \cos 2P'$$

$$S2P = \alpha'_p \sin 2P'$$

and the inverse relationship is given by $$\cos 2\Psi = \frac{C2P - a''}{1 - a'' C2P} \quad (1.4)$$

$$\cos \Delta = \frac{b''}{\sqrt{1 - a''^2}} \frac{\sqrt{1 - C2P^2}}{S2P}$$

In this representation, for an ideal instrument, equations (1.2) and (1.4) reduce to the ideal relationship given by $$a = \frac{\cos 2P - \cos 2\Psi}{1 - \cos 2P \cos 2\Psi} \quad (1.5)$$

$$b = \frac{\sin 2P \cos \Delta \sin 2\Psi}{1 - \cos 2P \cos 2\Psi}$$

$$\cos 2\Psi = \frac{\cos 2P - a}{1 - a \cos 2P}$$

$$\cos \Delta = \frac{b}{\sqrt{1 - a^2}} \frac{|\sin 2P|}{\sin 2P}$$

Let PSI-DELTA $\Psi_m, \Delta_m$ represent the spectra that is measured on an RAE device on a sample whose true spectra are represented by $\Psi, \Delta$. Currently most ellipsometer measurements are generated assuming the ideal relationships expressed by the equation set (1.5). As a result $$\cos 2\Psi_m = \frac{\cos 2P - a}{1 - a\cos 2P} \qquad (1.6)$$

$$\cos \Delta_m = \frac{b}{\sqrt{1-a^2}} \frac{|\sin 2P|}{\sin 2P}$$

The measured filter coefficients a, b are related to the true $\Psi, \alpha$ as expressed by equations (1.2), (1.3).

Thus, for a sample characterized by known $\Psi, \alpha$, the measured spectra on a specific RAE hardware characterized by the parameters described earlier can be predicted using equations (1.6),(1.2) and (1.3). This forms the basis for the inverse problem in which the true spectra and the measured spectra are known but the parameters characterizing the hardware are unknown.

As described in the previous section, the error spectrum can be predicted for a known set of hardware error $\Delta P_i$. To solve for hardware error $\Delta P_i$, given the measured spectrum, any regression scheme can be used. Conceptually, one can work directly with the measured spectra instead of the error spectra. In other words $$(\Psi_m, \Delta_m) = f(\Psi, \Delta, \Delta P_i)$$

The functional relationship is known given by (1.6), (1.2) and (1.3), and the true and measured spectra are known. Hence, the above equation is solvable to obtain the hardware error $\Delta P_i$ $$\Delta P_i \equiv \{dP, dA, \alpha_p, \alpha_a, \beta\}$$

Of these dP, dA are independent of the wavelength of light but the rest are wavelength dependent, and hence any regression scheme would be ineffective since the number of regression parameters is proportional to the problem size.

To overcome this problem, further analytic models were developed that reduce the parameter space. $\beta$ is modeled as a function of NA of the device and $\alpha$ is modeled as a function of the wire grid parameters to be discussed below. (The polarizers/analyzers used in ellipsometers are usually wire-grid polarizers). So the parameter space is substantially reduced, and one could also solve for the reduced $\Delta P_i$ by solving a set of matrix equations (each wavelength point data corresponding to one equation), say Gauss-Newton or Levenberg-Marquardt.

Once the hardware error parameters were known (by solving the inverse problem), the same functional relationship was used to predict the true spectra given the measured spectra and the hardware parameters.

However $\beta$ is not only a function of NA, but is also a function of the true reflection coefficients of the sample which are not known apriori and hence the need to have the iterative procedure described above.

The analytic expressions for the reflection and transmission coefficients derived for wire grid polarizers (WGP) are as follows.

Consider a plane wave incident on a grid with wire-radius a, wire-spacing d and wire-conductance $\sigma$. The electric field of the plane wave can be described by $$E_i(r) = E_0(\alpha' \hat{e}_x + \gamma' \hat{e}_z) \exp[-j(k \cdot r - \omega t)]$$

where $$k = k(\alpha \hat{e}_x + \beta \hat{e}_u + \gamma \hat{e}_z) \qquad (5.6)$$

The following conditions apply $$\alpha^2 + \beta^2 + \gamma^2 = \alpha'^2 + \beta'^2 + \gamma'^2 = 1$$

and $$\alpha\alpha' + \beta\beta' + \gamma\gamma' = 0$$

In the natural reference frame of the incident wave designated by (u, v, w) axes such that the wave-vector is oriented along the w axis, the electric field can be expressed as $$E_i(r) = E_0(\alpha'' \hat{e}_u + \beta'' \hat{e}_v) \exp[-j(kw - \omega t)] \qquad (5.7)$$

Further, using the following as eigen-vectors, the expressions for the reflection and transmission coefficients simplify considerably.

$$\hat{p}_1 = \frac{\beta \hat{e}_u + \alpha\gamma \hat{e}_v}{\sqrt{\beta^2 + \alpha^2\gamma^2}}, \hat{p}_2 = \frac{\beta \hat{e}_v - \alpha\gamma \hat{e}_u}{\sqrt{\beta^2 + \alpha^2\gamma^2}} \qquad (5.8)$$

Examination of the above eigenvectors shows that $p_1$ is parallel to the projection of the direction of the wires in the plane of the incident field. The components along these two eigen-directions are designated as $\parallel$ and $\perp$ respectively, the reflection and transmission coefficients of the grid are given by $$r_\parallel = -\frac{\lambda}{\pi d} \frac{(1-\alpha^2)}{\gamma} \frac{N_x}{\Delta_x} \qquad (5.9)$$

$$r_\perp = \frac{(1-\alpha^2)}{\gamma} \frac{a}{d} \frac{N_\theta}{\Delta_\theta} \qquad (5.10)$$

$$t_\parallel = 1 + r_\parallel \qquad (5.11)$$

$$t_\perp = 1 - r_\perp \qquad (5.12)$$

where $$N_x = 1 - j\frac{Z_s}{Z_0}\frac{ka}{2} \qquad (5.13)$$

$$\Delta_x = (1-\alpha^2)S_1 - j\frac{Z_s}{Z_0}\sqrt{1-\alpha^2}\, H_1^{(2)}(k'a) \qquad (5.14)$$

$$N_\theta = 1 + j\frac{Z_s}{Z_0}\frac{2}{ka} \qquad (5.15)$$

$$\Delta_\theta = \sqrt{1-\alpha^2}\, H_1^{(2)}(k'a) + j\frac{Z_s}{Z_0}(1-\alpha^2)S_1 \qquad (5.16)$$

and

-continued $$S_1 = H_0^{(2)}(k'a) + 2\sum_{n=1}^{\infty} H_0^{(2)}(k'nd)\cos(k\beta nd) \quad (5.17)$$

$$k' = k\sqrt{1-\alpha^2}$$

$$Z_s = (1+j)\sqrt{\frac{\mu_0 \omega}{2\sigma}}$$

$$Z_0 = \sqrt{\frac{\mu_0}{\varepsilon_0}},$$

where $\varepsilon_0$ and $\mu_0$ are the permittivity and permeability of free-space respectively; $Z_s$ is the surface impedance of the wires, $Z_0$ is the impedance of free-space and $H_m^{(2)}(x)$ is the Hankel function of the second kind of order m.

The above results are valid under the following assumptions $\lambda >> a$
$d >> a$
$Z_s << Z_0$ The convergence of the semi-infinite sum in the expression for $S_1$ is extremely slow. In addition to the above assumptions, in cases in which $d<<\lambda$, the sum can be analytically approximated using the following expression $$2\sum_{n=1}^{\infty} H_0^{(2)}(nx)\cos(bnx) \simeq$$

$$-1 + \frac{2}{x\sqrt{1-b^2}} + j\frac{2}{\pi}\left[C + \ln\left(\frac{x}{4\pi}\right) + \frac{x^2}{8\pi^2}(1+2b^2)\zeta(3)\right]$$

where C is Euler's constant and $\zeta(3)$ is a zeta function evaluated at 3 (i.e., the third order zeta function).

The Hankel functions can also be approximated as follows $$H_0^{(2)}(x) \simeq 1 - \left(\frac{x}{2}\right)^2 - j\frac{2}{\pi}\left\{\ln\left(\frac{x}{2}\right) + C + \left(\frac{x}{2}\right)^2\left[1 - \ln\left(\frac{x}{2}\right) - C\right]\right\} \quad (5.19)$$

$$H_1^{(2)}(x) \simeq \frac{x}{2} - j\left\{\frac{x}{\pi}\left[\ln\left(\frac{x}{2}\right) + C - 1\right] - \frac{2}{\pi x}\right\} \quad (5.20)$$

Once $t_\parallel$ and $t_\perp$ are evaluated, the attenuation coefficient of the polarizer can be evaluated as $$\alpha_p = \frac{T_\parallel}{T_\perp} = \frac{t_\parallel t_\parallel^*}{t_\perp t_\perp^*} \quad (5.21)$$

Using this model, the inverse problem can be solved and the grid parameters (a, d, σ) for a wire grid polarizer can be extracted.

Computer Implementation and Control

Figure 13:
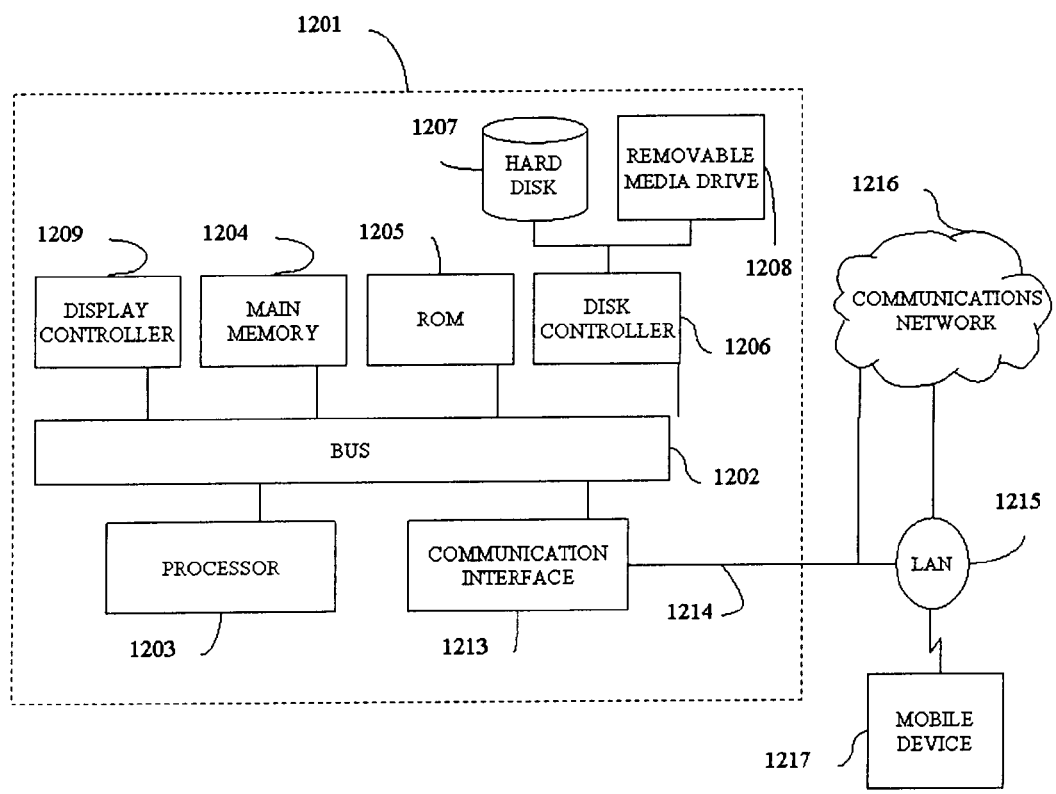
FIG. 13 illustrates a computer system for implementing various embodiments of the invention.

FIG. 13 illustrates a computer system 1201 for implementing various embodiments of the present invention. The computer system 1201 may be used as the metrology profiler system 53 to perform any or all of the functions described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of data stored and/or generated by the computer system 1201.

The computer system 1201 performs a portion or all of the processing steps of the invention (such as for example those described in relation to FIGS. 1, 4, and 5 and the programming of numerical analysis techniques for calculating the partial differential equations provided in the specification and accompanying figures) in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, or any other medium from which a computer can read.

Stored on any one or on a combination of computer readable media, the invention includes software for controlling the computer system 1201, for driving a device or devices for implementing the invention, and for enabling the computer system 1201 to interact with a human user (e.g., print production personnel). Such software may include, but is not limited to, device drivers, operating systems, development tools, and applications software. Such computer readable media further includes the computer program product of the invention for performing all or a portion (if processing is distributed) of the processing performed in implementing the invention.

The computer code devices of the invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213.

Processing Control with Systematic Error Correction

Figure 14:
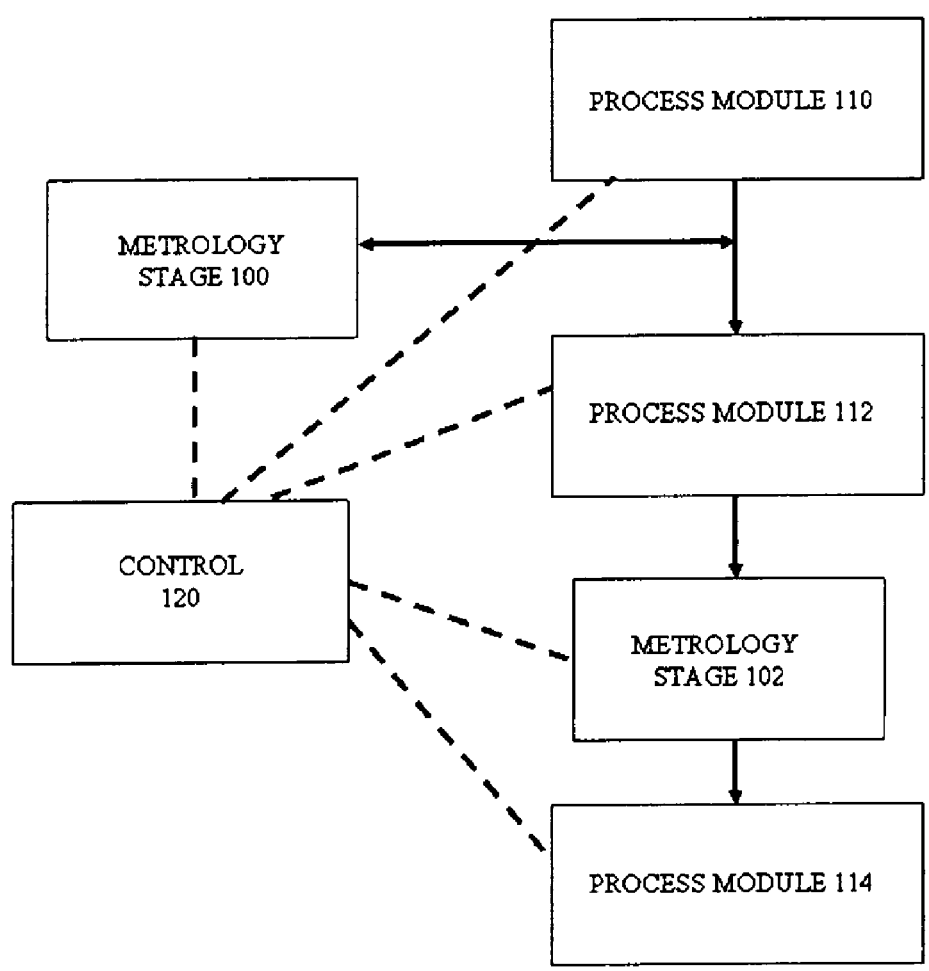
FIG. 14 is a schematic diagram showing an integrated process control system interfacing with a process reactor and an optical metrology tool.

FIG. 14 is a schematic diagram showing an integrated process control system interfacing with a process reactor and an optical metrology tool. As noted above, the present invention is in general applicable any metrology tool using an optical technique and feedback or feed forward for process control and in this embodiment is directed to integrated processing using what is termed hereafter a model-calibrated optical metrology tool.

As a noted earlier, it is important to not only ascertain the printed dimensions for quality assurance but also to use the dimensional information both in feed forward and feedback control. In the system shown in FIG. 14, process control is facilitated by transfer of wafers to and from various optical metrology stages 100 and 102 to various of the process modules 110, 112, and 114. A wafer handler 120 can exchange a substrate between the process modules 110, 112, and 114. As shown in FIG. 14, the process control can be facilitated by the placemen to optical metrology stages "in-line" with the wafer flow or can be facilitated by the transfer of wafers from the various stages to the designated metrology stages.

The metrology stages 100 and 102 can include the computer system 1201 for implementing various embodiments of the present invention, and specifically can include the metrology profiler system 53 described above. Furthermore, a central control system 120 can be used to control the wafer processing and archiving of the models and diagnostic data. In one embodiment of the present invention, a determination can be made for example by central control system 120 as to whether or not the hardware errors parameters $\Delta P_i$. need to be re-derived by introduction of the golden sample. Such recalibration may be necessary when there is a replacement of optical components in the optical metrology tool or if there are indications that the critical dimensions are drifting despite no apparent process variations.

The central control system 120 or any of the processors in the process modules 110, 112, and 114 or in the optical metrology stages 100 and 102 can be used to perform the above-noted feed forward control or feedback control or standards testing such as with the introduction of a golden wafer.

More specifically, the central control system 120 or any of the processors in the process modules 110, 112, and 114 or in the optical metrology stages 100 and 102 can be used to perform the following functions:

(1) measure a first diffraction spectrum from a standard substrate including a layer having a known refractive index and a known extinction coefficient by exposing the standard substrate to a spectrum of electromagnetic energy, (2) calculate a tool-perfect diffraction spectrum for the standard substrate, (3) calculate a hardware systematic error by comparing the measured diffraction spectrum to the calculated tool-perfect diffraction spectrum, (4) measure a second diffraction spectrum from a workpiece by exposing the workpiece to the spectrum of electromagnetic energy, and (5) correct the measured second diffraction spectrum based on the calculated hardware systematic error to obtain a corrected diffraction spectrum.

The central control system 120 or any of the processors in the process modules 110, 112, and 114 or in the optical metrology stages 100 and 102 can be used to determine a depolarization factor based on the standard substrate. Based on the depolarization factor, the corrected diffraction spectrum can be compared to a spectrum library to determining an interim spectrum match, and the corrected diffraction spectrum can be modified using the determined depolarization factor to form an iterate diffraction spectrum.

The central control system 120 or any of the processors in the process modules 110, 112, and 114 or in the optical metrology stages 100 and 102 can be used to repeat the comparing, the determining, and the modifying steps. Other functions include determining physical properties of the workpiece based on the iterate diffraction spectrum, and determining physical properties of the workpiece based on the corrected diffraction spectrum. Still other functions include measuring the first diffraction spectrum by measuring a psi-delta data set, calculating the tool-perfect diffraction spectrum by calculating a tool-perfect psi-delta data set; and calculating the hardware systematic error by comparing the measured psi-delta data set to the tool-perfect psi-delta data set.

The central control system 120 or any of the processors in the process modules 110, 112, and 114 or in the optical metrology stages 100 and 102 (1) can be used to calculate the hardware systematic error for at least one of an optical digital profilometry tool, an ellipsometric tool, and a reflectrometric tool, can measure a diffraction spectrum from a substrate having a single layer of dielectric, (2) can measure a diffraction spectrum from a substrate having a plurality of features of a known dimension (for example at least one of a sidewall angle, a film thickness, a column width, and a space between the plurality of features), (3) can measure a first diffraction spectrum in an integrated optical metrology system connected to a wafer processing tool, and (4) can calculate the tool-perfect diffraction spectrum by accounting for at least one of an analyzer azimuth, a polarizer azimuth, a wire grid radius, a wire grid spacing, a wire conductivity, and a numerical aperture.

The central control system 120 or any of the processors in the process modules 110, 112, and 114 or in the optical metrology stages 100 and 102 can be used to measure a first diffraction spectrum and measure a second diffraction spectrum by applying light from a single wavelength source or a broad wavelength source and by measuring diffracted light intensities as a function of angular diffraction (i.e., cosine delta). In one alternative, light can be applied from multiple single wavelength sources and diffracted light intensities can be measured as a function of angular diffraction. The diffracted light intensities can be measure for wavelengths of diffracted light from 175 nm to 33 μm (or from 190 nm to 830 nm, or from 400 nm to 800 nm). Light incident on the standard substrate or the workpiece can incident at angles from 0° to 90° (or 22.50 to 70°) of normal.

Other functions for the central control system 120 or any of the processors in the process modules 110, 112, and 114 or in the optical metrology stages 100 and 102 include (1) re-measuring the first diffraction spectrum, (2) re-calculating the a tool-perfect diffraction spectrum for the standard substrate, and (3) re-calculating the hardware systematic error in order to determine drifts in the optical measurement tool over time. Hence, the invention provides a way to monitor when and if recalibration of the optical measurement tool is needed. Still other functions include determining systematic errors in the optical metrology tool, for example by utilizing derived analytical expressions for at least one of optical component azimuth errors and optical component imperfections. The derived analytical expressions can be for at least one of optical component azimuth errors, optical component imperfections, and errors due to depolarization of light incident on the measured diffraction spectrum. These derived analytical expressions can be used to provide an inverse solution for the optical metrology tool, such as for example the rotating analyzer ellipsometer and the rotating compensator ellipsometer described above as well other optical measurement tools.

A plurality of embodiments for correcting systematic error in a metrology tool or a processing system using a metrology tool have been described. The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a device side (or active surface) of a substrate or integrated circuit is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first layer "on" a second layer is directly on and in immediate contact with the second layer unless such is specifically stated; there may be a third layer or other structure between the first layer and the second layer on the first layer. The embodiments of a device or article described herein can be manufactured, used, or shipped in a number of positions and orientations.

Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

The invention claimed is:

1. An optical measurement system comprising:
   an optical measurement tool configured to expose a substrate to a spectrum of energy;
   the optical measurement tool including a detection unit configured to measure,
     a first diffraction spectrum from a standard substrate including a layer having a known refractive index and extinction coefficient by exposing the standard substrate to the spectrum of electromagnetic energy, and
     a second diffraction spectrum from a workpiece by exposing the workpiece to the spectrum of electromagnetic energy;
   a computational unit configured to calculate a tool-perfect diffraction spectrum for the standard substrate, compare the measured diffraction spectrum to the calculated tool-perfect diffraction spectrum to generate a calculated a hardware systematic error, and correct the measured second diffraction spectrum based on the calculated hardware systematic error to obtain a corrected diffraction spectrum.

2. The system of claim 1, wherein the computational unit is configured to:
   determine a depolarization factor based on the standard substrate.

3. The system of claim 1, wherein the computational unit is configured to:
   compare the corrected diffraction spectrum to a spectrum library to determining an interim spectrum match; and
   modify the corrected diffraction spectrum using the depolarization factor to form an iterate diffraction spectrum.

4. The system of claim 1, wherein the computational unit is configured to determine physical properties of the workpiece.

5. The system of claim 1, wherein the computational unit is configured to:
   measure the first diffraction spectrum by analyzing data from a psi-delta data set;
   calculate the tool-perfect diffraction spectrum by calculating a tool-perfect psi-delta data set; and
   calculate the hardware systematic error by comparing the measured psi-delta data set to the tool-perfect psi-delta data set.

6. The system of claim 1, wherein the optical measurement tool comprises at least one of an ellipsometric tool and a reflectrometric tool.

7. The system of claim 6, further comprising:
   plural optical measurement tools connected to a wafer processing tool as an integrated optical metrology system.

8. The system of claim 1, wherein the optical measurement tool comprises an optical profilometry tool.

9. The system of claim 8, wherein the optical profilometry tool is configured to determine at least one of a sidewall angle, a film thickness, a column width, and a space between a plurality of features on the workpiece.

10. The system of claim 1, wherein the optical measurement tool comprises a detector to analyze diffracted light for various wavelengths.

11. The system of claim 10, wherein the detector is configured to measure wavelengths of diffracted light from 175 nm to 33 μm.

12. The system of claim 10, wherein the detector is configured to measure angles of diffracted light ranging from 22.5° to 70° of normal.

13. The system of claim 10, wherein the optical measurement tool is configured to apply light incident to the workpiece at angles from 0° to 90° of normal.

14. The system of claim 10, wherein the optical measurement tool comprises at least one of a single wavelength source and a broad wavelength source.

15. The system of claim 10, wherein the optical measurement tool comprises multiple single wavelength sources.

16. A semiconductor wafer processing tool comprising:
   a wafer handler which exchanges a substrate between plural wafer processing units; and
   an optical measurement system associated with the wafer handler and including,
     an optical measurement tool configured to expose the substrate to a spectrum of energy, and
     the optical measurement tool including a detection unit configured to measure,
       a first diffraction spectrum from a standard substrate including a layer having a known refractive index and extinction coefficient by exposing the standard substrate to the spectrum of electromagnetic energy, and
       a second diffraction spectrum from a workpiece by exposing the workpiece to the spectrum of electromagnetic energy, and
     a computational unit configured to calculate a tool-perfect diffraction spectrum for the standard substrate, compare the measured diffraction spectrum to the calculated tool-perfect diffraction spectrum to generate a calculated hardware systematic error, and correct the measured second diffraction spectrum based on the calculated hardware systematic error to obtain a corrected diffraction spectrum.

17. The wafer processing tool of claim 16, wherein the computational unit is configured to determine a depolarization factor based on the standard substrate.

18. The wafer processing tool of claim 17, wherein the computational unit is configured to:
   compare the corrected diffraction spectrum to a spectrum library to determining an interim spectrum match; and
   modify the corrected diffraction spectrum using the depolarization factor to form an iterate diffraction spectrum.

19. The wafer processing tool of claim 16, wherein the computational unit is configured to determine physical properties of the workpiece.

20. The wafer processing tool of claim 16, wherein the computational unit is configured to:
   measure the first diffraction spectrum by analyzing data from a psi-delta data set;
   calculate the tool-perfect diffraction spectrum by calculating a tool-perfect psi-delta data set; and
   calculate the hardware systematic error by comparing the measured psi-delta data set to the tool-perfect psi-delta data set.

21. The wafer processing tool of claim 16, wherein the optical measurement tool comprises at least one of an ellipsometric tool and a reflectrometric tool.

22. The wafer processing tool of claim 16, wherein the optical measurement tool comprises an optical profilometry tool.

23. The wafer processing tool of claim 22, wherein the optical profilometry tool is configured to determine at least one of a sidewall angle, a film thickness, a column width, and a space between a plurality of features on the workpiece.

24. The wafer processing tool of claim 22, further comprising:

plural optical measurement tools connected to a wafer processing tool as an integrated optical metrology system.

25. The wafer processing tool of claim 16, wherein the optical measurement tool comprises a detector to analyze diffracted light for various wavelengths.

26. The wafer processing tool of claim 25, wherein the detector is configured to measure wavelengths of diffracted light from 175 nm to 33 µm.

27. The wafer processing tool of claim 25, wherein the detector is configured to measure angles of diffracted light ranging from 22.5° to 70° of normal.

28. The wafer processing tool of claim 16, wherein the optical measurement tool is configured to apply light incident to the workpiece at angles from 0° to 90° of normal.

29. The wafer processing tool of claim 16, wherein the optical measurement tool comprises at least one of a single wavelength source and a broad wavelength source.

30. The wafer processing tool of claim 16, wherein the optical measurement tool comprises multiple single wavelength sources.

* * * * *